(12) United States Patent
Core et al.

(10) Patent No.: US 8,849,633 B2
(45) Date of Patent: Sep. 30, 2014

(54) METHOD AND APPARATUS FOR SELECTING A TRACKING METHOD TO USE IN IMAGE GUIDED TREATMENT

(75) Inventors: Matthew A. Core, San Jose, CA (US); Calvin R. Maurer, Jr., Mountain View, CA (US); Jay B. West, Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 193 days.

(21) Appl. No.: 13/281,386

(22) Filed: Oct. 25, 2011

(65) Prior Publication Data

US 2012/0109608 A1 May 3, 2012

Related U.S. Application Data

(60) Provisional application No. 61/455,984, filed on Oct. 29, 2010.

(51) Int. Cl.
*G06G 7/48* (2006.01)

(52) U.S. Cl.
USPC ............... 703/6; 378/18; 378/65; 600/427

(58) Field of Classification Search
USPC ............... 703/6; 378/8, 18, 65, 195; 382/132; 600/1, 315, 426, 427, 437; 606/130
See application file for complete search history.

(56) References Cited

U.S. PATENT DOCUMENTS

| | | | |
|---|---|---|---|
| 5,398,684 A | 3/1995 | Hardy | |
| 6,326,963 B1 | 12/2001 | Meehan | |
| 6,496,598 B1 | 12/2002 | Harman | |
| 6,867,773 B2 | 3/2005 | Hux | |
| 7,227,925 B1 | 6/2007 | Mansfield et al. | |
| 2002/0049375 A1 | 4/2002 | Strommer et al. | |
| 2004/0015073 A1 | 1/2004 | Schell et al. | |
| 2005/0059887 A1* | 3/2005 | Mostafavi et al. | 600/427 |
| 2005/0096515 A1* | 5/2005 | Geng | 600/315 |
| 2005/0180544 A1* | 8/2005 | Sauer et al. | 378/195 |
| 2006/0036170 A1* | 2/2006 | Lachaine et al. | 600/437 |
| 2006/0050847 A1 | 3/2006 | Jaffray et al. | |
| 2006/0100509 A1* | 5/2006 | Wright et al. | 600/426 |
| 2006/0291621 A1* | 12/2006 | Yan et al. | 378/65 |
| 2007/0071176 A1 | 3/2007 | Main et al. | |
| 2007/0127845 A1 | 6/2007 | Fu | |
| 2007/0274577 A1 | 11/2007 | De Font-Reaulx-Rojas | |
| 2008/0130825 A1* | 6/2008 | Fu et al. | 378/8 |
| 2008/0177279 A1* | 7/2008 | Sumanaweera et al. | 606/130 |
| 2008/0298540 A1* | 12/2008 | Serban et al. | 378/18 |
| 2009/0052623 A1* | 2/2009 | Tome et al. | 378/65 |

(Continued)

OTHER PUBLICATIONS

Tang et al., Fiducial Registration from a Single X-Ray Image: A New Technique for Fluoroscopic Guidance and Radiotherapy, S.L.Delp, A.M. DiGiogia, and B. Jaramaz (Eds.): MICCA/2000, LNCS 1935, 2000, pp. 502-511.

(Continued)

*Primary Examiner* — Kandasamy Thangavelu

(74) *Attorney, Agent, or Firm* — Lowenstein Sandler LLP

(57) ABSTRACT

A treatment delivery system or a simulation system simulates treatment of a patient, including testing the ability of one or more tracking methods to track a target position during the simulation. The system then presents simulation results to a user, the simulation results indicating whether any of the one or more tracking methods will successfully track the target position during treatment delivery.

27 Claims, 14 Drawing Sheets

(56) References Cited

U.S. PATENT DOCUMENTS

| | | |
|---|---|---|
| 2009/0110145 A1* | 4/2009 | Lu et al. .................. 378/65 |
| 2009/0180678 A1* | 7/2009 | Kuduvalli et al. ............ 382/132 |
| 2011/0107270 A1 | 5/2011 | Wang et al. |
| 2011/0166407 A1* | 7/2011 | Sumanaweera et al. .......... 600/1 |

OTHER PUBLICATIONS

Rhode et al., Registration and Tracking to Integrate X-Ray and MR Images in an XMR Facility, IEEE Transactions on Medical Imaging, Nov. 2003, pp. 1369-1378, vol. 22, No. 11.

Supplementary European Search Report for European Patent Application No. 08870643.7, dated Dec. 30, 2010, 14 pages.

Dongshan Fu, et al., Xsight Lung Tracking System: A Fiducial-Less Method for Respiratory Motion Tracking:, Jan. 1, 2007, Treating Tumors that Move with Respiration, Springer, DE, pp. 264-282, XP009142170, ISBN: 978-3-540-69885-2.

Yelin Suh et al., "Geometric uncertainty of 2D projection imaging in monitoring 3D tumor motion:," Physics in Medicine and Biology, Taylor and Francis Ltd. London, GB, vol. 52, No. 12, Jun. 21, 2007, pp. 3439-34554, XP020112919, ISSN: 0031-9155.

Khamene A. et al., "Automatic registration of portal images and volumetric CT for patient positioning in radiation therapy:," Medical Image Analysis, Oxford University Press, Oxford, GB, vol. 10, No. 1, Feb. 1, 2006, pp. 96-112, XPO25154071, ISSN: 1361-8415.

Zhiping Mu et al., "Multiple Fiducial Identification Using the Hidden Markov Model in Image Guided Radiosurgery:," Computer Vision and Pattern Recognition Workshop, 2006 Conference on New York, NY, USA, Jun. 17-22, 2006, Piscataway NJ, USA, IEEE, Piscataway, NJ, USA, Jun. 17, 2006, pp. 92-92, XP010922904.

BrainLAB: "IGRT ExacTrac® Brochure", Oct. 15, 2007, XP002613785, URL: http://web.archive.org/web/20071015153601/www.brainlab.com/downlowad/pdf/IGTExacTracBrochure.pdf (retrieved on Dec. 10, 2012).

Communication dated Jan. 18, 2011 for European Patent Application No. 08870643.7, 1 page.

Ross I. Berbeco, Steve B. Jiang, Gregory C. Sharp, George T.Y. Chen, Hassan Mostafavi, Hiroki Shirato, "Integrated radiotherapy imaging system (IRIS): design considerations of tumour tracking with linac gantry-mounted diagnostic x-ray systems with flat-panel detectors", Institute of Physics Publishing, Physics in Medicine and Biology, PH: S0031-9155 (04)683565-5, Phys. Med. Biol. 49 (2004) pp. 243-255.

PCT Internatinoal Search Report and Written Opinion of the International Searching Authority mailed Mar. 20, 2009 for serial No. PCT/US08/13644 filed Dec. 11, 2008, 10 pages.

USPTO Office Action dated Jul. 25, 2011 for U.S. Appl. No. 12/199,293.

USPTO Notice of Allowance dated Aug. 25, 2011 for U.S. Appl. No. 12/199,293.

Keall, P.J. et al. (Oct. 2006). "The Management of Respiratory Motion in Radiation Oncology Report of AAPM Task Group 76a)," Medical Physics 33(10):3874-3900.

Giraud, P. et al. (Mar. 2006). "Reduction of Organ Motion Effects in IMRT and Conformal 3D Radiation Delivery by Using Gating and Tracking Techniques," Cancer Radiotherapie 10:269-285.

Kilby, W. et al. (Oct. 2010). "The CyberKnife Robotic Radiosurgery System in 2010," Technology in Cancer Research and Treatment 9(5):433-452.

International Search Report and Written Opinion mailed Apr. 23, 2012, for PCT Patent Application No. PCT/US2011/058416, filed Oct. 28, 2011, 10 pages.

\* cited by examiner

METHOD AND APPARATUS FOR SELECTING A TRACKING METHOD TO USE IN IMAGE GUIDED TREATMENT

RELATED CASES

This patent application claims the benefit under 35 U.S.C. §119(e) of U.S. Provisional Application No. 61/455,984, filed Oct. 29, 2010, which is herein incorporated by reference.

TECHNICAL FIELD

Embodiments of the present invention relate to the field of image guided treatment and, in particular, to a system for identifying the eligibility of a tracking method to use in image guided treatment and for determining an optimal tracking method to use in image guided treatment.

BACKGROUND

In some medical applications, it may be necessary to dynamically track targets that move with time. For example, in radiation treatment it may be desirable to dynamically track tumors and/or lesions in the human body that move with respiration and/or heartbeat. In radiation treatment, accurate trajectories of the radiation beams through the patient anatomy to the lesion or tumor being treated can be critical, in order to achieve the radiation dose distribution that was computed during treatment planning time. For regions of the human anatomy that move, for example due to breathing or heartbeat, it is important to take such motions into consideration during treatment planning. Dynamic tracking may also be useful in applications other than radiation treatment in which parts of the anatomy move, due to breathing, heartbeat, or any other type of motion.

There are multiple different techniques that can be used to track a pathological anatomy (e.g., tumor or lesion) during treatment. Some tracking techniques have a high chance of success (e.g., a low chance that the anatomy's location will be reported incorrectly or that it's position will be undeterminable using the tracking technique), but a low accuracy, thereby requiring treatment of an increased amount of healthy tissue to ensure treatment of the full pathological anatomy. Other tracking techniques have lower chances of success, but a high accuracy. Therefore, when the tracking successfully works, less healthy tissue is treated.

One challenge in image guided treatment, such as radiation treatment, is determining which tracking technique to use for a patient. In conventional radiation treatment systems, a physician determines a tracking method to use for a patient based primarily on that physician's personal knowledge and expertise. Conventional treatment planning systems and treatment delivery systems do not include tools for performing simulation, testing potential tracking methods during the simulation, or analyzing simulation results to identify optimal tracking methods for tracking a target in the patient. Accordingly, some users create a treatment plan under an assumption that a particular tracking method will work, and later discover at treatment time that he cannot treat the patient because the chosen tracking technique cannot successfully track the pathological anatomy. This necessitates the generation of an entire new treatment plan, which wastes a medical physician's time, and adds considerable cost to treatment of the patient. For other patients, users generate treatment plans based on less than optimal tracking methods, i.e., methods providing less conformality (the degree to which a radiation dose matches the shape and extent of the target) and/or accuracy than other or optimal tracking methods, because users have good certainty the tracking method will work. The resulting sub-optimal treatment plan results in delivery of unnecessary radiation to healthy tissue.

BRIEF DESCRIPTION OF THE DRAWINGS

The present invention is illustrated by way of example, and not by way of limitation, in the figures of the accompanying drawings.

DETAILED DESCRIPTION

Figure 1:
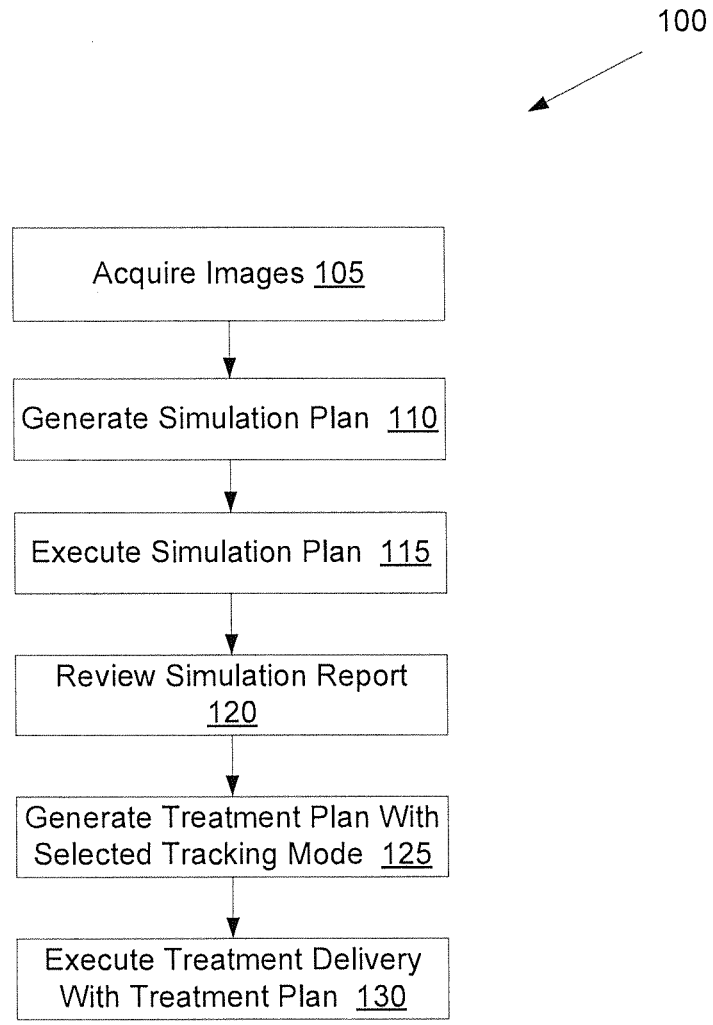
FIG. 1 illustrates a flow diagram for a method of selecting a tracking method and treating a patient using the selected tracking method, in accordance with one embodiment of the present invention.

Described herein is a method and apparatus for aiding a physician in the selection of a tracking method for use in image guided treatment, such as radiation treatment. Tracking, as used herein, means the ability to use an imaging modality (e.g., x-ray) to monitor/identify some or all components of the location of a target (e.g., tumor or lesion) within a body for the purpose of delivering some treatment to the target (e.g., radiation). Radiation treatment includes both radiation surgery (radiosurgery) and radiation therapy (radiotherapy). Radiotherapy and radiosurgery differ in the amount of radiation delivered to a patient in a treatment session. The amount of radiation in an individual session or fraction utilized in radiotherapy treatment sessions is typically about an order of magnitude smaller, as compared to the amount used in a radiosurgery session. For convenience, the term "radiation treatment" is used herein to mean radiosurgery and/or radiotherapy unless otherwise noted by the magnitude of the radiation.

In one embodiment, a single tracking method is simulated for a patient. This may include creating models (e.g., respiration models), imaging and tracking a target in a treatment device or a simulation device, correlating image data, and assessing results (e.g., determining the success or failure of tracking modes). Once the simulation is complete, simulation results answer the question, "can this patient be tracked with this tracking method?" In another embodiment, multiple tracking methods are simulated for the patient. Once the simulation is complete, the simulation results answer the question, "given a set of tracking methods, which is the optimal tracking method?"

To test a tracking method, multiple images are acquired during simulation using that tracking method. Image correlation is performed for each of the acquired images. The tracking method is then considered to have successfully tracked the target during the simulation if a successful correlation was performed for a threshold number of the images that were acquired using that tracking method. For example a tracking method may be considered to have successfully tracked the target during simulation if image correlation was successful for 75% of acquired images. In one embodiment, image correlation is performed by matching pattern intensity from digitally reconstructed radiographs (DRRs) to the images acquired using the tracking method.

Embodiments of the present invention describe treatment planning systems and treatment delivery systems that include automated tools for performing simulation, testing potential tracking methods during the simulation, and analyzing simulation results to verify performance of a tracking method and/or identify optimal tracking methods to use for a patient. These embodiments may allow for a potential reduction of total radiation delivered to healthy tissue, by identifying an optimal tracking method to use during treatment delivery. In addition, these embodiments may eliminate the occurrence of treatment plans having tracking methods that do not work for a particular patient, thereby reducing treatment costs by ensuring that physicians only need to develop a single treatment plan for a patient.

One clinical area in which it is important to accurately track the position of a target is radiation treatment of a lung tumor. For an average patient, a lung tumor will change position and/or shape throughout the patient's respiratory cycle. For simplicity and convenience, the following description will refer to radiation treatment of a lung tumor. However, it should be understood that the methods and systems described herein may also be used for image guided treatment of other areas of the body, such as the pancreas, liver, prostate, etc. Therefore, radiation treatment of a lung tumor is merely one example of an image guided treatment to which embodiments of the present invention can be applied.

FIG. 1 illustrates a flow diagram of a method 100 for selecting a tracking method and treating a patient using the selected tracking method. Method 100 is described in relation to treatment of a lung tumor. However, it should be understood that method 100 (as well as all other methods described herein) may also be used to select a tracking method for use in other treatments. In phase 105 of method 100, one or more images are acquired, for example and without limitation a computed tomography (CT) scan, magnetic resonance imaging (MRI) scans or positron emission tomography (PET) scans. For the purposes of this discussion, these images will be described as CT images, but may also be described as planning images (as physicians may use these images from which to create a treatment plan).

In one embodiment, at least two 3D CT images of the anatomy to be treated are acquired, preferably at the motion extremes of the anatomy. For example, a first CT image may be acquired while the patient holds his breath in an exhale position, and a second CT image may be acquired while the patient holds his breath in a full inhale position. This provides high quality images as well as a full range of motion to be expected of the lung tumor during respiration. Alternatively, a single CT image may be acquired, for example, if the tumor will move only slightly throughout the respiratory cycle. The skilled artisan will recognize the number and type of planning images required or desired for performing the simulation process of the present invention.

Alternatively, the physician acquires a 4D CT study, i.e., a CT scan taken over an extended period of time recording the positions of a moving volume over that extended period. The 4D CT study may define the entire motion range of the lung tumor, including the effects of hysteresis. However, it should be noted that the ability of the 4D CT study to give a complete view of motion during respiration should be balanced against the lower image quality typically provided by a 4D CT study as compared to a 3D CT image. In one embodiment, a 4D CT study is acquired along with a 3D CT image (e.g., a CT image taken while the user holds his breath in a full inhale position).

At phase 110 of method 100, a user generates a simulation plan for performing image guided treatment. The simulation plan may be configured to test one or multiple tracking methods and/or one or more treatment methods. Examples of tracking methods that may be tested by the simulation plan include 0-view tracking, 1-view tracking, 2-view tracking, and so forth. Examples of treatment methods include gated treatment and non-gated treatment. Detailed descriptions of some example tracking methods and treatment methods that may be tested are provided below.

Generating the simulation plan may include importing the acquired planning images, selecting one or more tracking methods to test, and generating a model that describes the tumor position and shape as a function of a phase of the respiration cycle and/or as a function of positions of external markers disposed on the patient. A simulation plan is similar to a radiation treatment plan, but has no dose attached to it, i.e., no actual radiation treatment of a patient may occur as a result of executing the simulation plan. The simulation plan may be generated by a therapist (rather than a physician) since there is no radiation dose associated with the simulation plan, resulting in a cost savings. Additionally, the physician may use the simulation plan as the basis for creating the actual treatment plan. Phase 110 is described in greater detail below with reference to FIG. 2.

At phase 115, a user executes the simulation plan. The simulation plan may be executed on a treatment delivery system, or on a simulation system (i.e., incapable delivering radiation). The simulation system comprises a treatment couch and an imaging system matching the actual treatment configuration, and may be the actual treatment system. Therefore, simulation results achieved on the simulation system closely or exactly match those that would be achieved with the treatment delivery system. Executing the simulation plan includes attempting to track the tumor using each of the selected tracking methods. Phase 115 is described in greater detail with reference to FIG. 3.

At phase 120, a user reviews a result of the simulation, and may select a tracking mode. The simulation results identify a measure of success for each of the tested tracking methods, and may indicate those tracking methods that successfully tracked the tumor position during the simulation. The simulation results may also rank the tracking methods based on degree of tracking success and/or tracking method accuracy and conformality. The review phase may be performed multiple times. For example, the review phase may be performed once by a technician when the simulation is complete, and again when a physician reviews the simulation results. The simulation report that is reviewed includes sufficient information to allow a decision maker (e.g., the physician) to confidently choose a tracking method. This may include a data set summary page that shows a number of images, number of successful correlations for each tracking mode, a recommended tracking mode, recommended algorithm parameters, couch offset, x-ray technique, and user notes. The reviewer may also open an x-ray technique selection page to view x-ray technique data in greater detail. Additionally, the reviewer may open an offset specification page to review offset data in greater detail and a correlation page to view correlation data in greater detail. The reviewer may select a tracking mode to use during treatment, and the selected tracking mode may be saved to the simulation plan.

At phase 125, a user generates a treatment plan with the selected tracking mode. A radiation treatment plan is a plan for the delivery of radiation treatment beams to the pathological anatomy of the patient from a number of treatment locations, with one or more beams (having one or more shapes, angles or orientations, energies, etc.) being applied from each location. Examples of treatment delivery systems include gantry based systems (manufactured by Siemens®, Varian®, Elekta®, or Mitsubishi®) or robotically mounted linac systems (manufactured by Accuray® Incorporated). The radiation treatment plan includes the selected tracking method, which may call for acquisition of a number and/or timing of intra-treatment diagnostic x-ray images, which are used to track the location of the target; diagnostic x-ray images being one example of intra-treatment data collected to track the position of the target. For example, and without limitation, diagnostic x-ray images are registered (as known by the skilled artisan) with pre-treatment 3D image data using digitally reconstructed radiographs or with cone beam CT scans. Moreover, the tracking method may include an imaging protocol that identifies, for example, an imaging modality to use (e.g., single x-ray projections, multiple x-ray projections, etc), an imaging algorithm or algorithms to use, whether to track fiducials or patient anatomy, etc. The term "x-ray image" as used herein may mean a visible x-ray image (e.g., displayed on a video screen) or a digital representation of an x-ray image (e.g., a file corresponding to the pixel output of an x-ray detector).

At phase 130, a user performs treatment delivery with the generated treatment plan (which includes the selected tracking mode).

Figure 2:
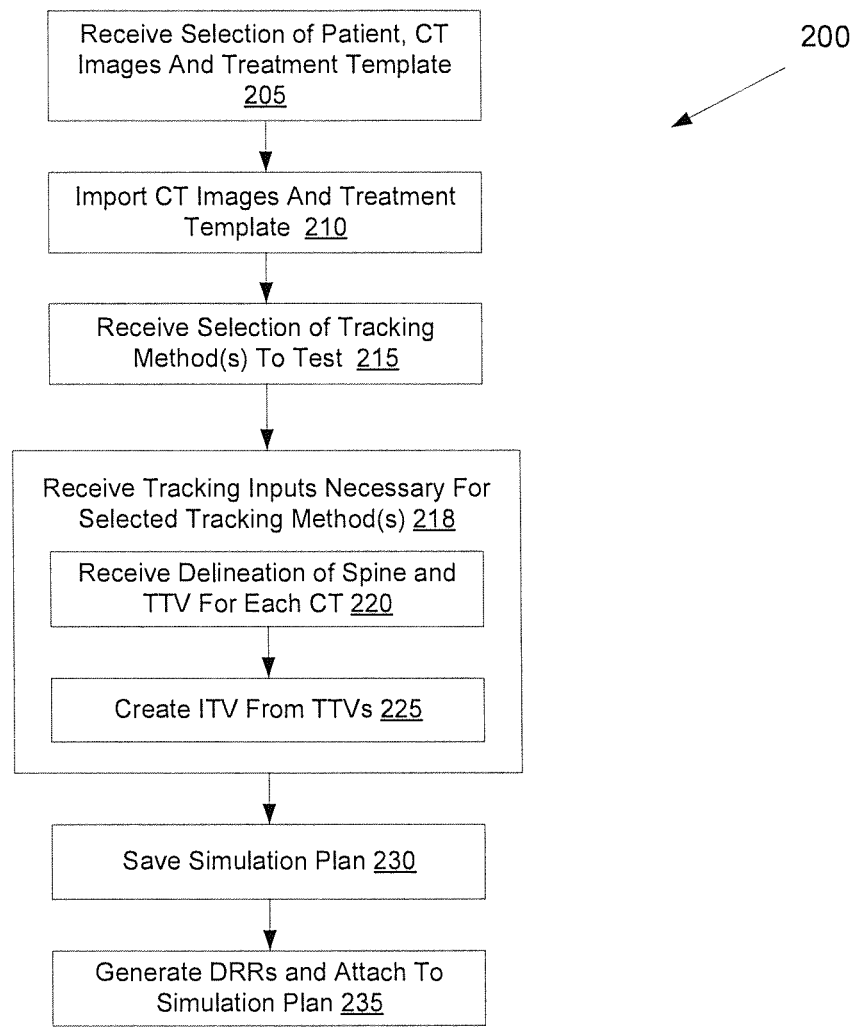
FIG. 2 illustrates a method of developing a simulation plan, in accordance with one embodiment of the present invention.

FIG. 2 illustrates a method 200 of developing a simulation plan, in accordance with one embodiment of the present invention. In one embodiment, method 200 is performed by a treatment simulator. The treatment simulator may be, without limitation, a simulation application that runs on a treatment planning system, a treatment delivery system, or a treatment simulation system.

At block 205 of method 200, the treatment simulator receives selection of a patient and one or more CT images (e.g., an inhale CT image and an exhale CT image). At block 210, the treatment simulator imports the selected CT images, which may be referred to as planning CTs. In one embodiment, the user is asked to designate one of the imported CT images as a primary CT. The treatment simulator may later use the primary CT to generate, for example, a preliminary estimate of the target position, as understood by the skilled artisan. The treatment simulator may also receive a selection of and load a treatment template. A treatment template provides one or more pre-defined treatment planning parameters and settings applicable to the anatomical treatment region of interest. For example, a lung tumor template may include instructions for delineating particular VOIs, for generating a model of a respiration cycle (as is done with the Accuray Synchrony® product) correlating tumor motion with external marker motion due to the respiration cycle. In one embodiment, the treatment template is a model treatment plan on which the simulation plan is based.

At block 215, the treatment simulator receives a selection of one or more tracking methods to test. Examples of tracking methods include x-ray imaging tracking methods that use a single x-ray image to track the tumor (1-view), methods that use two stereoscopic x-ray images to track the tumor (2-view), methods that use two stereoscopic x-ray images to track a structure (e.g., a skeletal structure) that has a known offset from the tumor (0-view), etc. Note that x-ray imaging tracking methods are described herein as a preferred embodiment. However, it should be understood that other tracking methods may also be included in the simulation, and that this disclosure should not be limited to x-ray imaging tracking methods.

At block 218, a user is asked to provide tracking inputs that are necessary for the selected tracking methods. This may include delineating volumes of interest (VOIs) such as target volumes and reference structures that will be used in tracking. The treatment simulator provides tools for a user to delineate these volumes. In one embodiment, at block 220, the treatment simulator receives a delineation of a spine and a tracking target volume (TTV), which may be the tracked tumor, for each imported CT image. The TTV may be considered to be similar to the Gross Target Volume (GTV), which is the extent of the treatment target visible in the CT image. However, the TTV differs from the GTV in that it may have small extensions and spiculations removed, for the reason that these small extensions and spiculations are not visible in the images produced during treatment and hence are not useful in terms of tracking.

At block 225, the treatment simulator creates an internal target volume (ITV) from the TTVs. The internal target volume is the volume defined by a target (e.g., by the TTV) as it moves through its full motion range. Thus, the ITV includes the entire motion range for the TTV (covering every position for the tumor along all three axes). In one embodiment, the ITV includes a margin expansion to compensate for setup inaccuracy, gross patient movement during treatment, and/or change of breathing pattern between planning and treatment. The ITV may be used for a tracking method that tracks tumor position based on a position of a reference structure such as the spine or other bone structure (referred to herein as 0-view tracking since no images of the tumor itself are being used to track the tumor's location). The 0-view tracking method, however, comes with the drawback of exposing larger volumes of normal tissue with prescription doses of radiation, especially in cases where the tumor undergoes a large excursion during breathing.

In addition to an ITV, one or more projected-ITVs may also be generated. Projected-ITVs may include the range of motion of the TTV along a single axis (e.g., an axis that is normal to an image plane). The projected-ITV for an axis is generated in the same way as an ITV, but using only the component of target motion along that axis. Projected-ITVs may be generated for up to two axes, corresponding to imaging axes of diagnostic x-ray imagers. Each projected-ITV may be used for a tracking method that tracks lung tumor position in a single imaging plane (referred to as 1-view tracking). Motion normal to that imaging plane cannot be tracked using a 1-view tracking method. Accordingly, the projected-ITV provides the entire motion range along the axis that cannot be tracked. A 1-view tracking method may be used, for example, when a tumor is only trackable in one imaging plane (e.g., if the tumor is occluded by another anatomical structure in the other imaging plane). When a 1-view tracking method is used, target locations are found in 2D. 2D coordinates are converted to 3D coordinates by projecting the 2D target position onto a plane that is parallel to a plane that intersects a treatment center, which is referred to as the treatment plane. In one embodiment, the treatment plane is determined based on offset information that identifies an offset between the spine and a centroid of the TTV.

In addition to an ITV, one or more truncated-ITVs may also be generated. The truncated-ITVs may include a subset of the range of motion of the TTV. The truncated-ITV is generated in the same way as an ITV, but using only a desired subset of motion rather than the full motion range of the TTV. The rationale for creating a truncated-ITV is that some radiation delivery systems have a "gating" mode, where the radiation beam is switched off whenever the target is deemed, by direct measurement or implicit measurement (e.g. by means of a correlation model, or monitoring the respiratory phase) to have moved outside a predefined spatial range. In this case, only motion of the TTV within the predefined range needs to be accommodated in the ITV.

The concepts of projected-ITV and truncated-ITV may be combined, to address the instance in which motion in one more axes is tracked, and motion in the remaining axes is constrained to be within a predefined range.

At block 230, the treatment simulator saves the simulation plan. Saving the simulation plan may include saving projection contours for the TTV, saving projection contours for the ITV and/or projected-ITVs, saving a spine alignment CT center and/or a lung tracking CT center, and/or saving additional information. At block 235, the treatment simulator generates a set of digitally reconstructed radiographs (DRRs) from the CT image data, and adds the DRRs to the saved simulation plan. The DRRs are generated using the same beam projection geometries as will be used to acquire x-ray images during simulation.

It should be noted that the time required to generate a simulation plan is considerably shorter than the time required to generate a treatment plan. A treatment plan requires a physician to contour a clinical volume, and requires a series of treatment delivery optimizations to be performed. However, a simulation plan does not need any clinical volumes, nor does it require any treatment delivery optimizations. For example, it may take about 5-30 minutes to develop a simulation plan and multiple hours to develop a treatment plan, and, as mentioned previously, a non-physician can create a simulation plan because no dose can be prescribed or delivered when running the simulation.

Figure 3:
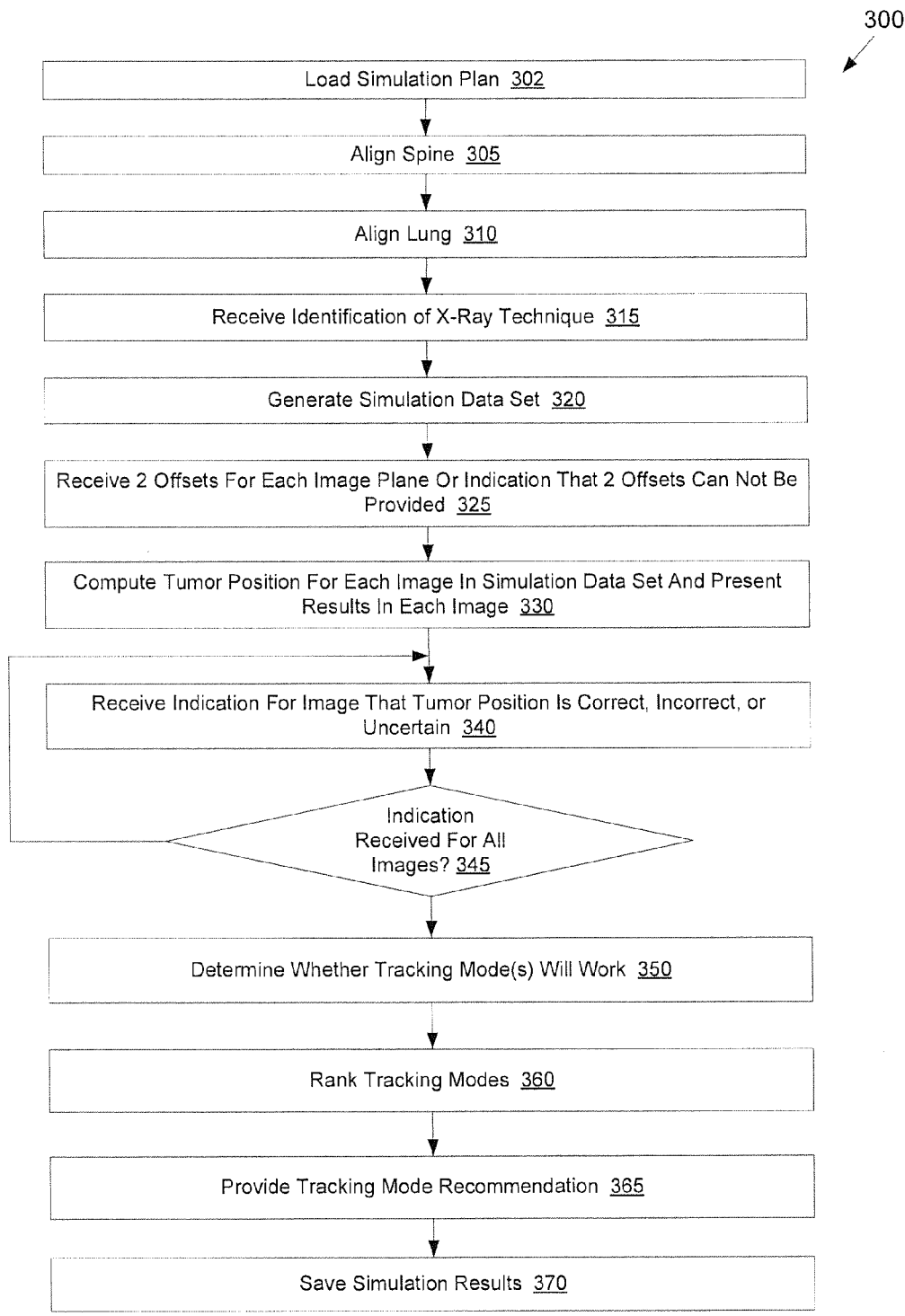
FIG. 3 illustrates a method of executing a simulation plan to identify the feasibility of using one or more tracking methods during treatment, in accordance with one embodiment of the present invention.

FIG. 3 illustrates a method 300 of executing a simulation plan to identify the feasibility of using one or more tracking methods during treatment, in accordance with one embodiment of the present invention. In one embodiment, method 300 is performed by a treatment simulator. The treatment simulator may be software that runs on a treatment delivery system or a treatment simulation system set up to mimic the treatment delivery system. By executing the simulation plan, the treatment simulator is able to identify which tracking methods are suitable for use during patient treatment.

At block 302 of method 300, a user loads a simulation plan (e.g., the simulation plan generated at method 200) into the treatment simulator. The patient is then placed on a treatment couch, and x-ray images are taken of the patient. The treatment couch has six degrees of freedom of position in a preferred embodiment, and so can be rotated about three axes and moved along three axes. At block 305 of method 300, the treatment simulator receives user inputs that adjust the couch position to align the patient's spine to a treatment center. Alternatively, the treatment simulator may receive user inputs to align another reference structure to the treatment center. In a preferred embodiment, the spine alignment is performed by aligning DRRs generated from the CT images with the x-ray images taken during the simulation. The couch may be repositioned multiple times, and a new pair of x-ray images may be taken after each repositioning. The alignment is complete when the treatment simulator determines that the alignment has only small residual corrections. In one embodiment, alignment is complete when the alignment is correct to within +/−10 mm in translations along each axis, +/−1 to +/−1.5 degrees in pitch, +/−1 to +/−1.5 degrees in roll and +/−1 to +/−3 degrees in yaw. There are known methods and mechanisms for aligning the patient using the spine, for example Xsight® Spine made by Accuray Incorprated.

At block 310, after spine alignment is complete, the treatment simulator receives a user input to align the patient's lung (or other anatomy if a lung tumor were not being treated). This may cause the couch to automatically change position so that the patient's lung is approximately at the treatment center. The user may then make minor corrections to align the lung as described with reference to spine alignment. Once the alignment is complete, the tumor's motion range should be centered at the treatment center. Note that alignment for a moving tumor involves understanding the motion range of the target tumor, and positioning the patient so that the center of that range of motion is aligned to the treatment center. In one embodiment, the system assists users in performing this alignment by enabling the user to acquire x-ray images at motion extremes (e.g., inhale and exhale points).

The method then continues to block 315 provided that an x-ray has been acquired since a last couch position change was performed. In one embodiment, external markers (e.g., light emitting diodes (LEDs)) should be attached to the patient before the method continues to block 315. In one embodiment, the method will not continue to block 315 until at least one external marker has been continuously visible for 3 or more consecutive respiratory cycles. The external markers are used to track the patient's respiratory cycle. A model may be generated that correlates positions of the external markers to phases of the patient's respiratory cycle, and ultimately to tumor location and/or shape, for example such as is done by Accuray Incorporated's Synchrony® Tracking System. The respiration model describes a non-rigid motion and deformation of the anatomical region as it undergoes its periodic motion (e.g. due to respiration). The respiration model relates the locations of the targets to the locations of the external markers, as a function of the relative position in time within the respiration cycle. The respiration model may be constructed from the CT images and from motion cycle information obtained from sensors that track the external markers. The respiration model may be created during generation of the simulation plan and/or during simulation.

At block 315, the treatment simulator receives an indication of an x-ray technique. The x-ray technique includes voltage (kV), exposure time (ms) and current (mA). Increasing the kV parameter increases the energy of the photons emitted by the x-ray sources, which in turn increases their penetrating power. Changing this parameter alters the differential contrast between different types of tissue, e.g. bone, fat, and muscle tissue. Increasing the current and/or the time parameters increases the number of photons emitted, thereby increasing the signal reaching a detector. Determination of the x-ray technique may be an iterative process, in which a user selects an x-ray technique, refines the x-ray technique, and further refines the x-ray technique until the final x-ray technique provides sufficient x-ray images to match with the generated DRRs. In one embodiment, a histogram of image intensity is provided for an x-ray image pair generated using a current x-ray technique. If the histogram shows a range that is narrower than a range threshold, then a user may be instructed to modify the x-ray technique. In one embodiment, a separate x-ray technique is determined for each x-ray imager.

At block 320, the treatment simulator generates a simulation data set using the identified x-ray technique. The simulation data set includes multiple x-ray image pairs, each x-ray image pair including an x-ray image generated by a first x-ray imager (imager A) and an x-ray image generated by a second x-ray imager (imager B). Each x-ray image pair may be taken at a different phase of the patient's respiration cycle. In one embodiment, the patient's respiration cycle is divided into 8 separate phases, and may include 8-12 image pairs taken across the patient's respiration cycle. In one embodiment, images are acquired beginning at the maximum inspiration and expiration points of the patient's respiration cycle. Additional images are then taken moving inwards towards the center of the respiration cycle. This ordering can potentially reduce the number of images required before a user can complete offset specification (described below). Acquisition of the image pairs may be based on monitoring external markers on a patient's chest to track the respiratory cycle. As each image pair in the image data set is generated, it may be displayed to a user. Note that the images may be taken during multiple different respiration cycles (e.g., if imaging hardware cannot take all of the images within a single respiration cycle).

At block 325, the treatment simulator receives preliminary tumor position information identifying an initial estimate of the tumor position. This estimate is defined using the alignment of the spine and the known separation in the planning CT between the spine and the tumor volume, and may include translation information along three axes defining that separation. A user may supplement the initial position estimate by providing offset information, i.e., a manual estimate of the tumor position in one or more images. This offset information may be supplied while the simulation data set is still being generated (e.g., before block 320 has finished), so long as at least one image pair has been generated. In one embodiment, the user selects an image in which to provide the offset information, the image having been taken at a particular phase in the patient's respiratory cycle. The treatment simulator displays a graphical delineation of the lung tumor in the image, the graphical delineation having a shape appropriate to the phase in the patient's respiration cycle in which the image was taken. The user is asked to drag the delineation to where they see the tumor in the image, thereby providing the offset information. The offset information is received for up to two images in each image plane or projection. It should be noted that the image A offsets and the image B offsets do not need to be identified for the same image pair(s). For example, a user might provide image A offsets for image pairs 1 and 4, but image B offsets for image pairs 2 and 6. In one embodiment, the user is requested to provide offset information for images that are spread apart in the respiration cycle (e.g., one image at one of the three phase points nearest each end of the respiration cycle). This will ensure enough difference in position of the tumor so that a model used to determine tumor location for the other images can be accurate.

If a user cannot see the tumor in two images for a particular image plane, the treatment simulator receives an indication from the user that the treatment volume is not visible, and one or more tracking methods may automatically be disqualified as candidates for use during treatment. For example, if a tumor is not viewable in an image plane, 3D tracking of the tumor using two x-ray images (referred to as 2-view tracking) will not be possible, and 2D tracking of the tumor using the image plane in which the tumor is not visible will not be possible.

At block 330, the treatment simulator computes a tumor position for each image in the simulation data set. The tumor position for an image may be determined based on the respiration model, the positioning of the external markers when the image was taken, and/or the positioning of the patient's spine when the image was taken. The tumor position may also be determined via correlation with a DRR (or other computed image) generated based on the CTs and the respiration model. In one embodiment, the correlation is performed based on performing image correlation/registration between a DRR and the x-ray image. The image registration may be performed using pattern intensity or other known or to be determined techniques. In one embodiment, the treatment simulator uses a gradient-based algorithm to attempt to locate the tumor in each image.

As used herein, image correlation is defined as an attempt to create a computed image (e.g., digitally reconstructed radiograph (DRR)) that matches an image taken during treatment or during simulation (also referred to herein as "acquired image"), and then to use all or part of the computed image to identify a target in the acquired image. To perform image correlation, a system identifies a target in a computed image and identifies a region in the acquired image displaying an intensity pattern in some manner similar to that of the target in the computed image. Generation of the computed image and computation of the target position/shape may be based on a preoperative 3D image, a respiration model, a phase of a patient's respiratory cycle in which the image was taken and/or the positions of external markers when the image was taken. Performing the image correlation may include identifying and/or computing a digitally reconstructed radiograph (DRR) that shows a target position that matches the position of the target in the acquired image. An image correlation is successful if a computed image (e.g., a DRR) having a target position and/or shape that matches closely to the position and/or shape of the target in the acquired image is found. Typically, a user will make a final confirmation as to whether an image correlation was successful.

In one embodiment, a correlation confidence metric is used to gauge the success of image correlation. The confidence metric is a measure of how well the target region in the computed image matches the corresponding region in the acquired image. If the confidence metric for the image correlation of a particular image is below a threshold level, the correlation is considered to have failed for that image. If the confidence metric for the image correlation of the image is at or above the threshold, the correlation is considered to have succeeded for that image, subject to user confirmation.

Figure 9:
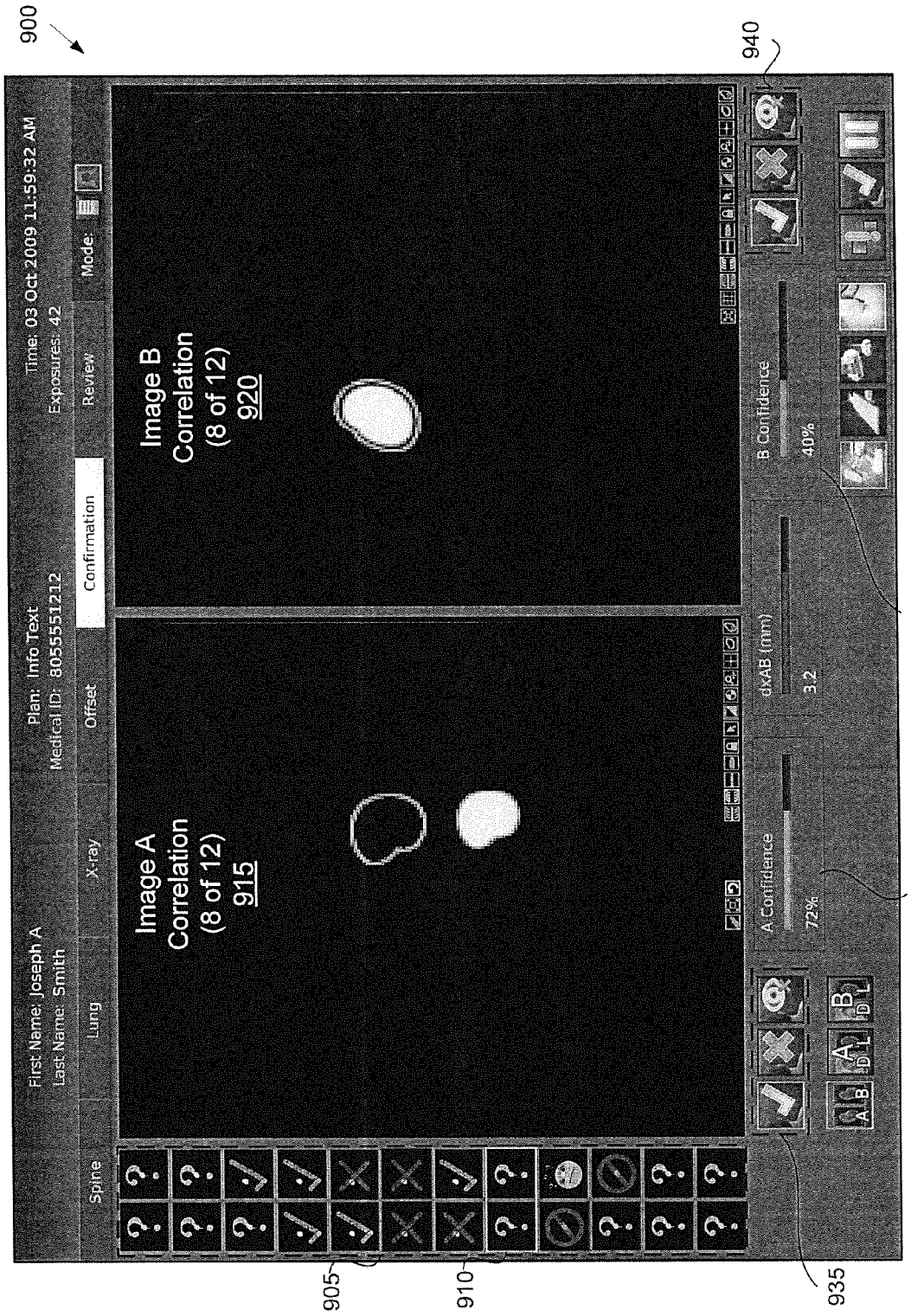
FIG. 9 illustrates a GUI of the data set correlation and user conformation phase task, in accordance with one embodiment of the present invention.

In one embodiment, each tumor position and/or correlation has a confidence metric associated with it. An example of a successful image correlation and an unsuccessful image correlation, and associated confidence metrics, is shown in FIG. 9, which is discussed below. The confidence metric in one embodiment is based on a tumor region matching method. A matching window for the image registration process contains the tumor and some surrounding background. If the matching window has shifted slightly in any direction, the new window still includes most of the tumor plus some additional background. This new matching window may be referred to as a shifted matching window. Registration performed on the original matching window and on the shifted matching window should give the same or similar result. If the results are different, this indicates increased likelihood of an incorrect correlation between an observed target location (e.g., target in an x-ray image) and a computed target location (e.g., target in a DRR). Accordingly, the confidence metric can be computed by defining multiple shifted matching windows, each offset from the nominal tumor position by a different amount. A small search window centered at the position of the tumor detected in the x-ray image is then defined by the original matching window. Registration is repeated for each shifted matching window, and the differences from the original translation are calculated. Detection confidence is then determined based on the percentage of shifted matching windows with small differences from the original translation. If the confidence metric for the tumor position correlation in a particular image is below a threshold level, the correlation is considered to have failed for that image. The treatment simulator will indicate for each image whether there was a successful correlation or a failed correlation. In one embodiment, the treatment simulator presents tumor position correlation results to a user as they become available. Alternatively, tumor position correlation results may not be displayed until they have been computed for all image pairs.

At block 340, the treatment simulator receives an indication for an image that the tumor position correlation was successful, unsuccessful, or that success is indeterminate. The user may make such a determination by viewing the images, which include the correlation information. If a computed shape and position of the tumor overlaps the tumor in the acquired image accurately, the user can provide the indication that the correlation was successful. If the computed shape and/or location of the tumor do not overlap the tumor in the image, the user can provide an indication that the correlation was unsuccessful. At block 345, the treatment simulator determines whether an indication has been received for all images (including images from both image planes). If an indication has not been received for all images, the method returns to block 340. If an indication has been received for all images, the method continues to block 350.

At block 350, the treatment simulator determines whether one or more tracking modes are likely to work for tracking the tumor during treatment delivery. In one embodiment, a tracking mode is considered to have successfully tracked the target during the simulation if a successful correlation was performed for a threshold number of the images that are associated with the tracking mode. For example and without limitation, a tracking method may be considered to have successfully tracked the target during simulation if the image correlation was successful for 75% of the acquired images associated with that tracking mode. Examples of tracking modes include a 2-view x-ray tracking mode (in which 3D tracking is achieved using two stereoscopic x-ray images), a 1-view A x-ray tracking mode (in which 2D tracking is achieved using a single first or A x-ray image in a first image plane), a 1-view B x-ray tracking mode (in which 2D tracking is achieved using a single second or B x-ray image in a second image plane), and a 0-view x-ray tracking mode (in which the patient's spine is tracked and the location of the target is approximately known relative to the spine). The 2-view tracking mode may be associated with all acquired images. Therefore, the 2-view tracking mode may be considered to have successfully tracked the target during simulation if image correlation was successful for 75% of all acquired images. The 1-view A tracking mode may be associated with all images taken by a first detector. Therefore, the 1-view A tracking mode may be considered to have successfully tracked the target during simulation if image correlation was successful for 75% of the images acquired by the first detector. Similarly, the 1-view B tracking mode may be associated with all images taken by a second detector. Therefore, the 1-view B tracking mode may be considered to have successfully tracked the target during simulation if image correlation was successful for 75% of the images acquired by the second detector. In one embodiment, the 0-view x-ray tracking mode is considered to always be successful as long as successful correlation on images of the patient's spine was initially achieved.

At block 360, the treatment simulator ranks the tracking modes. The tracking modes may be ranked based on the percentage of images that each tracking mode successfully tracked, as well as the accuracy and conformality associated with each tracking mode. For example, the 2-view tracking mode, which uses stereoscopic imaging, may have an accuracy of approximately 1.5 mm in every dimension, and treatment may be delivered to a region that is highly conformal to the shape of the tumor. The 1-view tracking modes, which track in two dimensions, may have an accuracy of approximately 1.5 mm in the two tracked dimensions, and an accuracy of approximately 4-5 mm in the untracked dimension. To account for the inaccuracy in the untracked dimension, and because of target motion in the untracked dimension, the region treated in that dimension is larger than the tumor volume in that dimension, and therefore the 1-view tracking modes have a lower conformality than the 2-view tracking mode. For the 0-view tracking mode, the tumor is not tracked directly, and the accuracy in all dimensions is approximately 8-10 mm, which results in a lower conformality. In one embodiment, tracking modes that failed to successfully track the tumor in at least the threshold number of images are excluded from the ranking. Of those tracking modes that successfully tracked the tumor in at least the threshold number of images, the tracking modes may be ranked based on accuracy and/or conformality. For example, the 2-view tracking mode has an optimal combination of accuracy and conformality, the 1-view tracking modes are of intermediate accuracy and conformality, and the 0-view tracking mode has the lowest accuracy and conformality. Therefore, if all tracking modes were successful, the 2-view tracking mode would be given the highest rank.

At block 365, the treatment simulator provides a tracking mode recommendation. The recommendation may include information that a doctor can use to make a determination as to whether a particular tracking mode or multiple tracking modes will work. This information may include the percentage of images in which each of the tracking modes were successful. The recommendation may be based on the ranking generated at block 360. The user may then select the recommended tracking method or another tracking method for use during treatment.

In one embodiment, the recommendation includes a recommendation as to the viability of using fiducial tracking. A recommendation as to whether to track from the spine (e.g., using the 0-view tracking method) or to use a fiducial tracking method could be based on, for example, a location of the tumor. For example, if the tumor is near the heart, the large margins that are required for 0-view tracking may cause the heart to become irradiated, and thus the 0-view tracking method may be inadvisable. In one embodiment, the tracking mode ranking includes a ranking of both the fiducial tracking method and the 0-view tracking method. Each of these tracking methods may be considered to have approximately 100% tracking success, but may be ranked behind other methods due to complications and drawbacks associated with these tracking methods.

At block 370, the treatment simulator then saves the simulation results, along with the selected tracking method. By executing the simulation plan, a user can eliminate false positives (where a doctor prescribes tracking method that doesn't work) and false negatives (where a doctor prescribes a less accurate tracking method than can be used).

Figure 4:
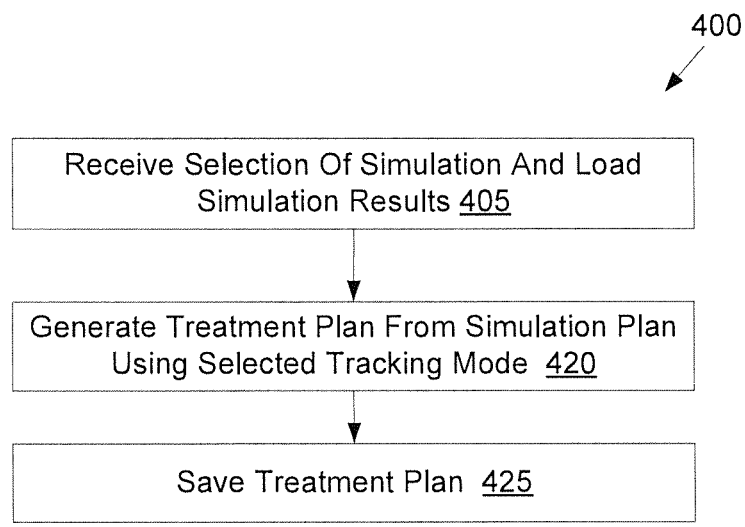
FIG. 4 illustrates a method of generating a treatment plan using a simulation plan and a selected tracking method, in accordance with one embodiment of the present invention.

FIG. 4 illustrates a method 400 of generating a treatment plan, in accordance with one embodiment of the present invention. In one embodiment, method 400 is performed by a treatment planning system, as described below. Alternatively, method 400 may be performed by a treatment delivery system.

At block 405 of method 400, the treatment planning system receives a selection of a completed simulation and loads a simulation plan along with simulation results. The tracking method selected for the simulation plan will be used for the treatment plan.

The contours created for the simulation plan are present, but may be labeled so as to prevent their use for treatment without physician review. If the selected tracking mode is a 1-view tracking mode, a user is asked to confirm which VOI holds the ITV, and which VOIs hold the projected-ITV. Note that treatment plans using different tracking modes may be incompatible. Therefore, a plan that has been generated using a first tracking method may not later be modified by switching tracking methods.

At block 420, a physician using the treatment planning system generates a treatment plan using the selected tracking mode. In one embodiment, the treatment planning system uses the simulation plan as an input during the treatment plan generation process. For example, the selected tracking method, x-ray techniques, offset information, etc. from the simulation plan may be used for generating a treatment plan. At block 425, the treatment planning system then saves the treatment plan. The patient may then undergo radiation treatment in a treatment delivery system using the treatment plan with the selected tracking method.

FIGS. 5-10 illustrate screenshots of a graphical user interface for a treatment simulator, in accordance with one embodiment of the present invention. The treatment simulator may be an application that runs on a treatment planning system and/or a treatment delivery system. In one embodiment, the treatment simulator is a module of a treatment planning system and/or a treatment delivery system.

In radiation treatment planning and delivery, interfaces are typically control consoles. From the control consoles, users have the ability to exercise all of the system hardware and invoke most any system interaction. The idea is that the user has a task, and is presented with a set of tools to accomplish this task. The GUIs shown in FIGS. 5-10 moves away from the control console concept, towards a wizard concept. As shown in FIGS. 5-10, the treatment simulation task is broken down into a series of individual actions that are to be performed. The decomposition falls into ordered tasks that require user control (e.g., due to hazard mitigation or steps that are difficult to perform automatically but that a user can perform trivially).

To simplify the user's understanding of the workflow described in method 300, a set of icons is used to describe the different simulation phases. Taking FIG. 5 as an example, the phase icons 505 are shown across the top of the GUI. From left to right, there are phase icons 505 for the spine alignment phase, lung alignment phase, x-ray technique specification phase, user offset provision phase, user results confirmation phase, and results review phase. Users can transition from phase to phase either through a workflow-centric "next" button, or by clicking directly on an icon associated with a particular phase. The currently active phase is indicated by a highlighted phase icon.

The GUIs include multiple buttons, which cause some action to be performed when pressed. In one embodiment, button color is used to convey meaning about the action that the button will perform. For example, four different color categories may be used to identify types of actions. In one embodiment, red buttons are action buttons, orange buttons are decision buttons, light blue buttons are information buttons and dark blue buttons are phase selection buttons. Clicking a button with a red background color will result in some system action, likely involving hardware or radiation. Clicking a button with an orange background color indicates a decision that a user is making inside the current phase. Clicking a button with the light blue background color does not change the state of the hardware or the current phase. Instead, clicking such a button provides the user with a different view of information or more detailed information. Clicking buttons with the dark blue background (the phase selection buttons) changes a current phase. In alternative embodiments, button size and/or shape are used instead of, or in addition to, color to differentiate between different action types.

The GUIs include system status icons 510 in the lower right hand corner of the display. The status icons 510 are software indicators of hardware devices. In one embodiment, the status icons 510 include a robot status icon 515 that identifies the state of a robot that controls the positioning of a linear accelerator (linac) that delivers a treatment radiation beam, a treatment couch status icon 520 that identifies the state of the treatment couch that holds the patient, a diagnostic imaging system icon 525 and a linac icon 530. The status icons are color coded based on current statuses of the hardware devices. In one embodiment, a blue background for a status icon indicates that a device is idle. An idle device will perform no actions unless a user interacts with the system. In one embodiment, a green background color indicates that a device is in an automation state (referred to herein as an armed state). While a device is armed, that device can become active at any time without any interaction from the user. The armed state warns the user that the user should be aware of the device since it can become active without the user interacting with the system. In one embodiment, an orange background color indicates that a device is active, and a yellow background color indicates that a device is active and delivering radiation.

Figure 5:
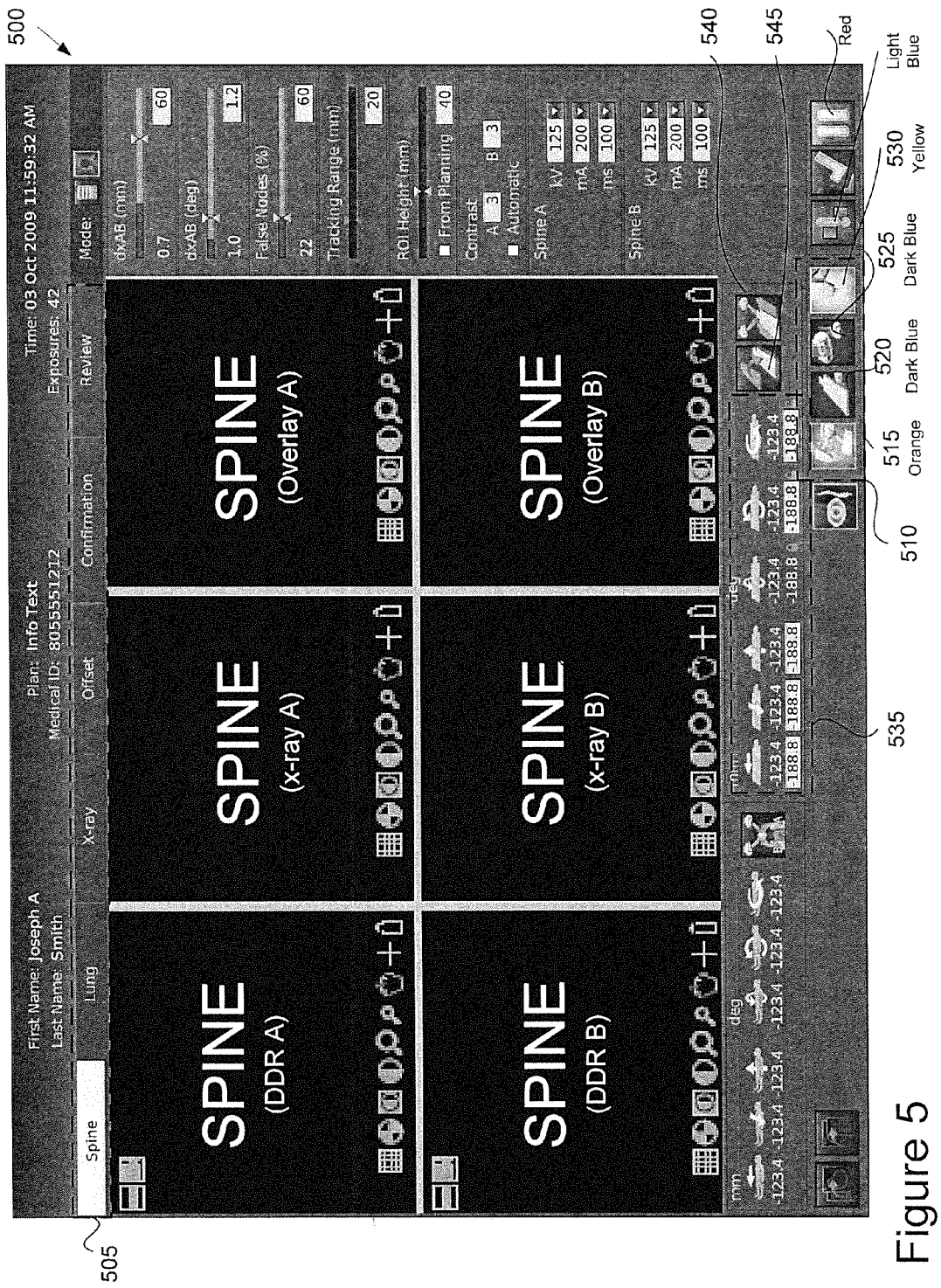
FIG. 5 illustrates a graphical user interface (GUI) of a spine alignment task for generating a simulation plan, in accordance with one embodiment of the present invention.

FIG. 5 illustrates a graphical user interface (GUI) 500 of a spine alignment task for generating a simulation plan, in accordance with one embodiment of the present invention, and as described at block 305 of method 300. The GUI 500 for the spine alignment task includes all of the tools that are necessary to accomplish spine alignment. In one embodiment, GUI 500 includes a pair of DRRs that were generated from a preoperative CT image. The pair of DRRs include DRR A, which reflects the same beam geometry of an x-ray image taken from a first x-ray imager (imager A) and DRR B, which reflects the same beam geometry of an x-ray image taken from a second x-ray imager (imager B). GUI 500 also includes a pair of latest x-ray images taken from imager A and imager B and an overlay of DRR A with x-ray image A (overlay A) and an overlay of DRR B with x-ray image B (overlay B). The overlay A and overlay B images indicate whether the spine has been properly aligned, or whether further position correction is required. GUI 500 further includes a set of couch position inputs 535 for adjusting the position (e.g., x, y, z) and rotation (e.g., r, p, w) of the couch to align the spine. A reposition button 545 moves the couch to updated position and rotation coordinates, and a take x-ray button 540 causes a new pair of diagnostic x-rays to be taken (e.g., a new x-ray A and x-ray B).

GUI 500 may also include buttons for turning on and off skeletal mesh and alignment center markers, inverting the images and changing window levels, zooming in and out, panning the images, and so on. Additionally, GUI 500 may identify various error metrics for a current correlation and an ability to change an error threshold. In one embodiment, GUI 500 also includes a button to perform automatic spine alignment.

Figure 6:
FIG. 6 illustrates a GUI of a lung alignment task for generating a simulation plan, in accordance with one embodiment of the present invention.

FIG. 6 illustrates a GUI 600 of a lung alignment task for generating a simulation plan, in accordance with one embodiment of the present invention, and as described at block 310 of method 300. GUI 600 includes all of the tools that are necessary to accomplish lung alignment. As in the spine alignment task, GUI 600 includes a pair of DRRs that was generated from a preoperative CT image, a pair of latest x-ray images taken from imager A and imager B, and an overlay of DRR A with x-ray image A and an overlay of DRR B with x-ray image B. The overlay A and overlay B images indicate whether the lung has been properly aligned, or whether further position correction is required.

GUI 600 includes a lung alignment button 610. When entering the lung alignment phase, the user is prompted to move to the lung alignment center (e.g., by flashing the lung alignment button 610 until it is pressed). When pressed, the lung alignment button 610 causes the couch to change positions so that the patient's lung becomes aligned to the treatment center. There is a known offset between the patient's spine and the patient's tumor. Therefore, once the spine has been aligned, the lung alignment button 610 may cause the system to automatically align the patient's tumor. In one embodiment, the center point of the ITV is aligned to the treatment center. In another embodiment, the average of the centers of the TTVs for the two CT images is aligned to the treatment center (e.g., if no ITV was defined). In another embodiment, the centroid of a single TTV is aligned to the treatment center (e.g., if only one CT image was taken).

Once the couch has been moved to the lung alignment position, the user is asked to acquire an image and visually align the patient. In one embodiment, the user is directed to align the patient based on anatomy that does not move significantly during the patient's respiration cycle. GUI 600 includes a set of couch position inputs 605 for adjusting the position (e.g., x, y, z) and rotation (e.g., r, p, w) of the couch to perform lung position alignment.

Figure 7:
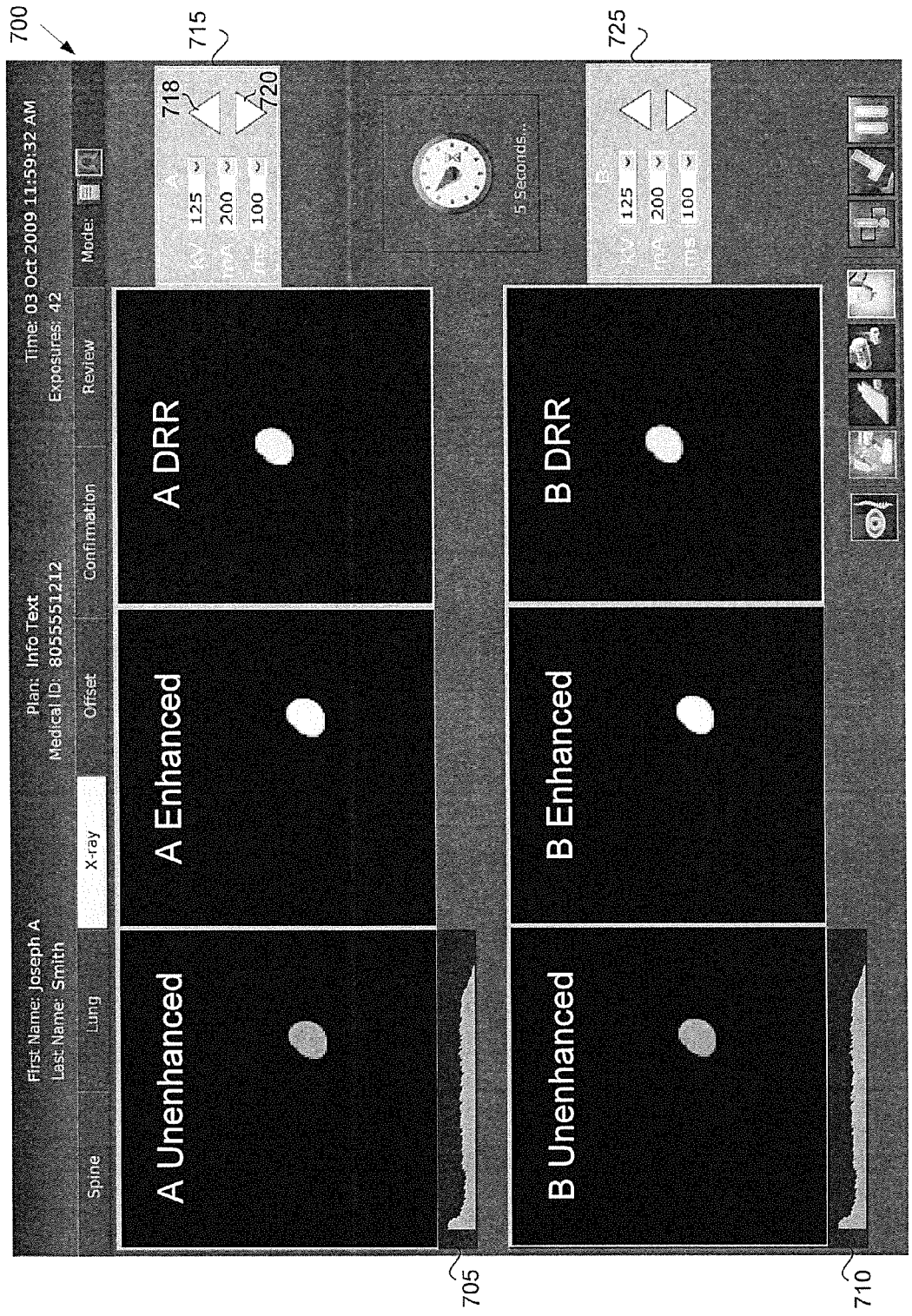
FIG. 7 illustrates a GUI of an x-ray technique selection task, in accordance with one embodiment of the present invention.

FIG. 7 illustrates a GUI 700 of an x-ray technique selection task, in accordance with one embodiment of the present invention, and as described at block 315 of method 300. GUI 700 includes all of the tools that are necessary to select an appropriate x-ray technique. In one embodiment, GUI 700 presents the user with unenhanced, enhanced and DRR images side by side for both A and B images. Histograms 705, 710 of pixel intensity may be shown under one or more of the displayed images. GUI 700 further includes controls 715 for changing the kV, mA, and ms settings for x-ray image A and controls 725 for changing the kV, mA, and ms settings x-ray image B. Users may separately change the settings for any of the kV, mA or ms settings. Some settings (such as those not attainable by the x-ray imagers) may not be allowed by the treatment simulator.

In one embodiment, users may use a "step-up" button 718 or "step-down" button 720, which change one or more of the kV, mA or ms settings automatically to increase or decrease the intensity of an x-ray image by an incremental amount. In one embodiment, the step up and step down controls automatically manage steps between kV and mA so that kV increases are minimized, which may maximize image quality. In one embodiment, the step up and step down controls do not modify the ms setting.

Note that the user may perform the x-ray technique selection phase out of sequence (e.g., before performing the spine or lung alignment phases). For example, if the current x-ray technique that is used to generate images that are shown in the spine alignment phase are poor, a user may jump to the x-ray technique phase to improve the x-ray technique, and then return to the spine alignment phase.

Figure 8:
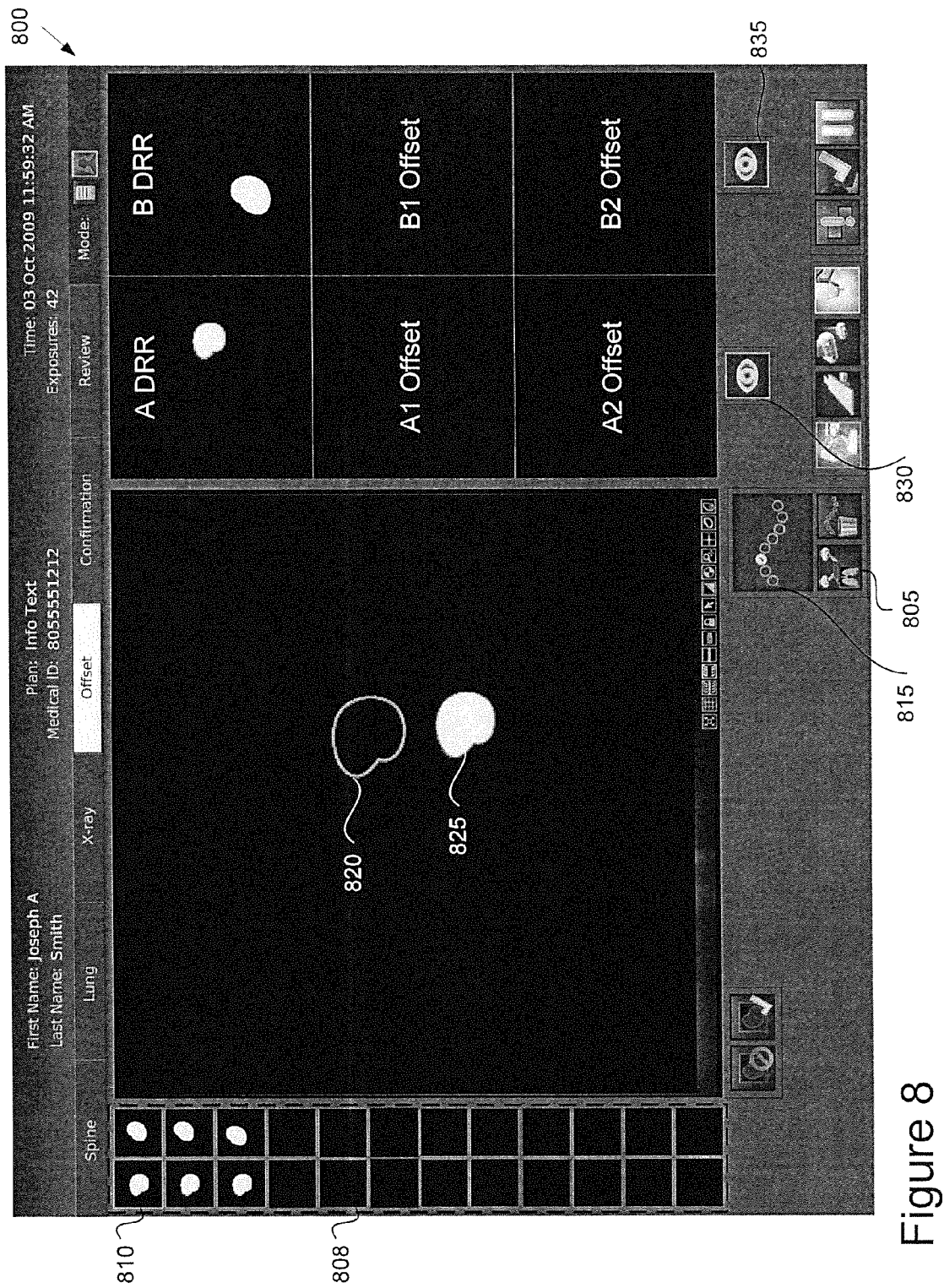
FIG. 8 illustrates a GUI of a data set acquisition and offset identification phase task, in accordance with one embodiment of the present invention.

FIG. 8 illustrates a GUI 800 of a data set acquisition and offset identification phase task, in accordance with one embodiment of the present invention, and as described at blocks 320 and 325 of method 300. The data set acquisition phase and offset identification phase are two of three potentially parallel phases that are designed to acquire and correlate a data set. The user begins the data set acquisition phase by clicking an acquire data set button 805. Provided there is no interruption (e.g., if external markers are not detectable by an external tracking system), the imaging system begins generating image pairs (each pair including an image A and an image B). While the data set acquisition control sequence runs in the background, the user is provided with the ability to identify offsets for one or more images that have already been generated in the GUI 800. New images are made available as they are taken.

As shown, the left hand side of the GUI 800 includes a film strip view 808 of the image pairs in the image set. The film strip 808 may simulate a movie. The images may be taken across multiple respiration cycles. For example, a single image may be taken every 2-3 respiration cycles. In one embodiment, the film strip 808 is ordered by time. Alternatively, the film strip 808 may be ordered by phase in the respiration cycle. Each of the images is taken during a known phase of the respiration cycle. Accordingly, to phase sort, the images simply need to be rearranged according to their known phase. The GUI 800 may include a button that goes through the images and loops, so that it appears that a user is going through a single respiration cycle. The GUI 800 may also include sort buttons for switching between a phase sort and a time sort.

In the film strip view 808 of image pairs, each image is either blank (indicating that the image for that slot has not yet been taken), or shows a thumbnail view of an x-ray image. A user may click on any of the images to perform offset identification for that image. For example, in the GUI 800 a first image A 810 has been selected (shown with a yellow border). First image A 810 was taken during a third phase of the respiration cycle, as indicated by a respiration phase icon 815 that has the third phase highlighted. A user sets the offset for the image by clicking and dragging an outline of the tumor 820 over the tumor 825 shown in the image. Once the tracking offsets have been committed in two images for both A and B, a correlate data set button becomes available. The user presses this button to proceed to the next phase. In some cases, the tumor may not be visible in two images for either A or B. If this is the case, the user may depress the "image not visible"

button for A or B, 830 and 835, respectively, after which he may proceed to the next phase.

FIG. 9 illustrates a GUI 900 of the data set correlation and user conformation phase task, in accordance with one embodiment of the present invention, and as described at blocks 340 and 345 of method 300. The data set correlation and user confirmation phase may be performed in parallel with the data set acquisition phase and the offset identification phase. The correlation is performed separately for each image once the offsets have been set and a user presses the correlation button. Correlation involves computing a position and shape of a target (e.g., a lung tumor) from a preoperative 3D image and/or a respiration model and correlating that computed position and shape to an observed position and shape for that target. As correlation is completed for an image pair, the correlation results for that image pair are displayed over the images in the film strip view 905 on the left. An image correlation may be successful (represented by a question mark) or unsuccessful (indicated by a circle with a slash through it). A correlation is unsuccessful if the correlation has a confidence metric that fails to meet a minimum threshold. The user goes through each image that was successfully correlated, and confirms whether he agrees that the image was successfully correlated.

In the illustrated example, correlations have completed for 12 image pairs, and the user has selected image pair 8 for confirmation (identified by a yellow border 910 in the film strip view 905). When an image pair is selected for confirmation, image A 915 and image B 920 from the image pair are displayed, the displays including the tumor location correlation. Each of the image A correlation 915 and the image B correlation 920 include a confidence metric, 925 and 930, respectively. The user visually reviews the image A correlation 915 and the image B correlation 920, and determines whether the correlation appears correct. For each image correlation, the user is provided buttons for confirming successful correlation, indicating that the correlation failed, or indicating an inability to determine whether the correlation has succeeded. Buttons 935 are provided for image correlation A and buttons 940 are provided for image correlation B.

In the film strip view 905, each image correlation that the user has confirmed is shown with an overlay of a check mark, each image correlation that the user has rejected is shown with an X, and each image in which the user was unable to identify whether the correlation was accurate is shown with, for example, a frowny face or an eye with an X.

Figure 10:
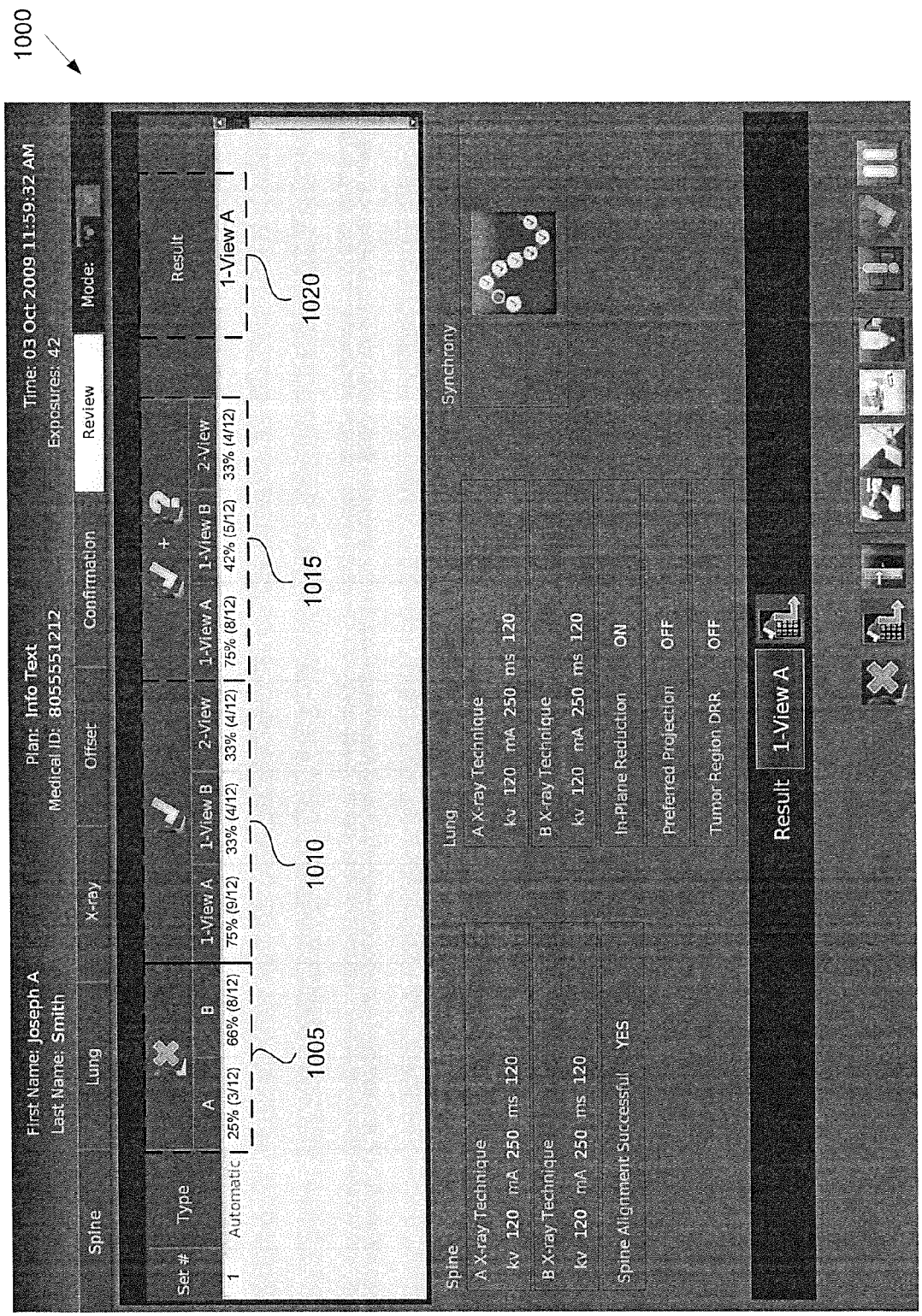
FIG. 10 illustrates a GUI of the simulation results review phase task, in accordance with one embodiment of the present invention.

FIG. 10 illustrates a GUI 1000 of the simulation results review phase task, in accordance with one embodiment of the present invention, and as described at block 120 of method 100. Once the user has completed the confirmation phase and elected to proceed, they will be presented with an overall summary of the data set correlation results, as shown. The results identify the percentage of A images and B images for which the correlation failed 1005. The results further identify the percentage of images for which each tested tracking mode was successful (e.g., the percentage of images associated with a particular tracking mode that were successfully correlated), exclusive of indeterminate findings 1010. The results also identify the percentage of image pairs for which each tested tracking mode was successful, inclusive of indeterminate findings 1015. Additionally, the GUI 1000 may include information on algorithm parameters used for correlation, x-ray techniques used for correlation, offset from spine to lung position, as used to acquire the images of the data set, identification of respiration phases represented by the images, and so on. In one embodiment, the GUI includes a tracking mode recommendation 1020. The GUI may also include an identification of the respiration phases that were successfully tracked (e.g., for which a successful correlation was confirmed by a user) using the recommended tracking mode. In the illustrated example, tracking mode 1-view A successfully tracked (e.g., identified and correlated) the tumor in 75% of the images, tracking mode 1-view B successfully tracked the tumor in 33-42% of the images, and tracking mode 2-view successfully tracked the tumor in 33% of the images. Accordingly, for this example the 1-view A tracking mode has been recommended for use during treatment. Note that the user may create more than one data set for a patient. Different data sets may be generated using different alignments, different offsets, different x-ray techniques, and so on. The review phase may include results for each of the completed data sets. These data sets may be ranked based on overall success rates. The completed simulation may be saved automatically, or upon user input.

Figure 11:
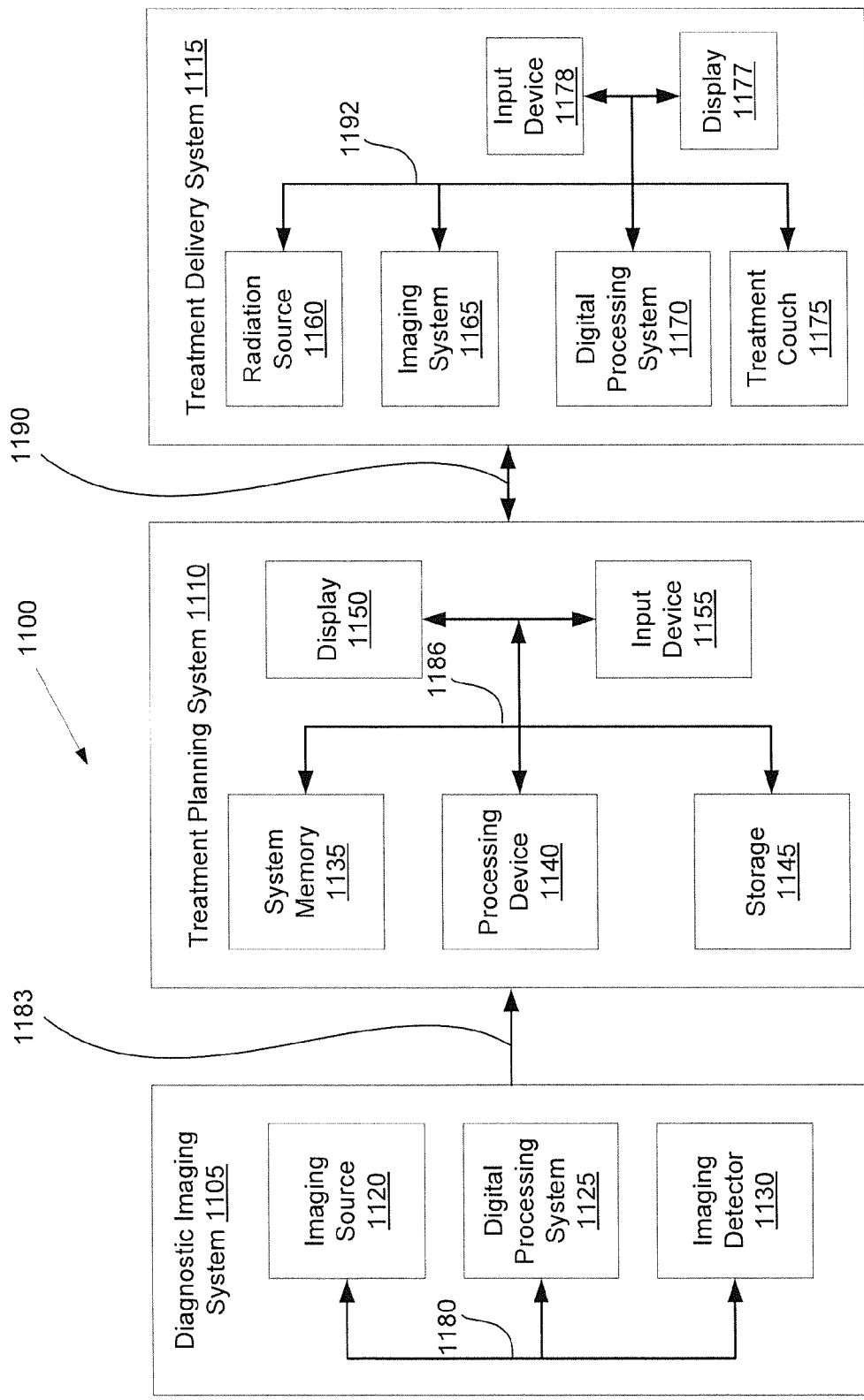
FIG. 11 illustrates one embodiment of systems that may be used in generating a simulation plan, performing simulation, and/or performing radiation treatment.

FIG. 11 illustrates one embodiment of systems that may be used in generating a simulation plan, performing simulation, and/or performing radiation treatment. These systems may be used to perform, for example, the methods described above. As described below and illustrated in FIG. 11, a system 1100 may include a diagnostic imaging system 1105, a treatment planning system 1110, a treatment delivery system 1115 and a motion detecting system (not shown). In one embodiment, the diagnostic imaging system 1105 and the motion detecting system are combined into a single unit.

Diagnostic imaging system 1105 may be any system capable of producing medical diagnostic images of a patient that may be used for subsequent medical diagnosis, treatment planning, treatment simulation and/or treatment delivery. For example, diagnostic imaging system 1105 may be a computed tomography (CT) system, a magnetic resonance imaging (MRI) system, a positron emission tomography (PET) system, or the like. For ease of discussion, diagnostic imaging system 1105 may be discussed below at times in relation to an x-ray imaging modality. However, other imaging modalities such as those above may also be used.

In one embodiment, diagnostic imaging system 1105 includes an imaging source 1120 to generate an imaging beam (e.g., x-rays) and an imaging detector 1130 to detect and receive the beam generated by imaging source 1120, or a secondary beam or emission stimulated by the beam from the imaging source (e.g., in an MRI or PET scan).

The imaging source 1120 and the imaging detector 1130 may be coupled to a digital processing system 1125 to control the imaging operation and process image data. In one embodiment, diagnostic imaging system 1105. In another embodiment, diagnostic imaging system 1105 may receive imaging commands from treatment delivery system 1115.

Diagnostic imaging system 1105 includes a bus or other means 1180 for transferring data and commands among digital processing system 1125, imaging source 1120 and imaging detector 1130. Digital processing system 1125 may include one or more general-purpose processors (e.g., a microprocessor), special purpose processor such as a digital signal processor (DSP) or other type of device such as a controller or field programmable gate array (FPGA). Digital processing system 1125 may also include other components (not shown) such as memory, storage devices, network adapters and the like. Digital processing system 1125 may be configured to generate digital diagnostic images in a standard format, such as the DICOM (Digital Imaging and Communications in Medicine) format, for example. In other embodiments, digital processing system 1125 may generate other standard or non-standard digital image formats. Digital processing system 1125 may transmit diagnostic image files (e.g., the aforementioned DICOM formatted files) to treatment delivery system 1115 over a data link 1183, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treat a patient despite the existence of a physical separation between the system user and the patient.

Treatment delivery system 1115 includes a therapeutic and/or surgical radiation source 1160 to administer a prescribed radiation dose to a target volume in conformance with a treatment plan. Treatment delivery system 1115 may also include a digital processing system 1170 to control radiation source 1160, receive and process data from diagnostic imaging system 1105 and/or motion detecting system 1106, and control a patient support device such as a treatment couch 1175. Digital processing system 1170 may be configured to register 2D radiographic images received from diagnostic imaging system 1105, from two or more stereoscopic projections, with digitally reconstructed radiographs (DRRs) generated by digital processing system 1125 in diagnostic imaging system 1105 and/or DRRs generated by processing device 1140 in treatment planning system 1110. Digital processing system 1170 may include one or more general-purpose processors (e.g., a microprocessor), special purpose processor such as a digital signal processor (DSP) or other type of device such as a controller or field programmable gate array (FPGA). Digital processing system 1170 may also include other components (not shown) such as memory, storage devices, network adapters and the like.

In one embodiment, digital processing system 1170 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 1170 may also include a storage device, representing one or more storage devices (e.g., a magnetic disk drive or optical disk drive) for storing information and instructions. The storage device may be used for storing instructions for performing the treatment delivery steps discussed herein. Digital processing system 1170 may be coupled to radiation source 1160 and treatment couch 1175 by a bus 1192 or other type of control and communication interface.

Digital processing system 1170 may implement methods to manage timing of diagnostic x-ray imaging in order to maintain alignment of a target with a radiation treatment beam delivered by the radiation source 1160.

In one embodiment, the treatment delivery system 1115 includes an input device 1178 and a display 1177 connected with digital processing system 1170 via bus 1192. The display 1177 can show trend data that identifies a rate of target movement (e.g., a rate of movement of a target volume that is under treatment). The display can also show a current radiation exposure of a patient and a projected radiation exposure for the patient. The input device 1178 can enable a clinician to adjust parameters of a treatment delivery plan during treatment.

Treatment planning system 1110 includes a processing device 1140 to generate and modify treatment plans and/or simulation plans. Processing device 1140 may represent one or more general-purpose processors (e.g., a microprocessor), special purpose processor such as a digital signal processor (DSP) or other type of device such as a controller or field programmable gate array (FPGA). Processing device 1140 may be configured to execute instructions for performing simulation generating operations and/or treatment planning operations discussed herein.

Treatment planning system 1110 may also include system memory 1135 that may include a random access memory (RAM), or other dynamic storage devices, coupled to processing device 1140 by bus 1186, for storing information and instructions to be executed by processing device 1140. System memory 1135 also may be used for storing temporary variables or other intermediate information during execution of instructions by processing device 1140. System memory 1135 may also include a read only memory (ROM) and/or other static storage device coupled to bus 1186 for storing static information and instructions for processing device 1140.

Treatment planning system 1110 may also include storage device 1145, representing one or more storage devices (e.g., a magnetic disk drive or optical disk drive) coupled to bus 1186 for storing information and instructions. Storage device 1145 may be used for storing instructions for performing the treatment planning steps discussed herein.

Processing device 1140 may also be coupled to a display device 1150, such as a cathode ray tube (CRT) or liquid crystal display (LCD), for displaying information (e.g., a 2D or 3D representation of the VOI) to the user. An input device 1155, such as a keyboard, may be coupled to processing device 1140 for communicating information and/or command selections to processing device 1140. One or more other user input devices (e.g., a mouse, a trackball or cursor direction keys) may also be used to communicate directional information, to select commands for processing device 1140 and to control cursor movements on display 1150.

Treatment planning system 1110 may share its database (e.g., data stored in storage 1145) with a treatment delivery system, such as treatment delivery system 1115, so that it may not be necessary to export from the treatment planning system prior to treatment delivery. Treatment planning system 1110 may be linked to treatment delivery system 1115 via a data link 1190, which may be a direct link, a LAN link or a WAN link.

It should be noted that when data links 1183, 1184 and 1190 are implemented as LAN or WAN connections, any of diagnostic imaging system 1105, treatment planning system 1110 and/or treatment delivery system 1115 may be in decentralized locations such that the systems may be physically remote from each other. Alternatively, any of diagnostic imaging system 1105, treatment planning system 1110, and/or treatment delivery system 1115 may be integrated with each other in one or more systems.

Figure 12:
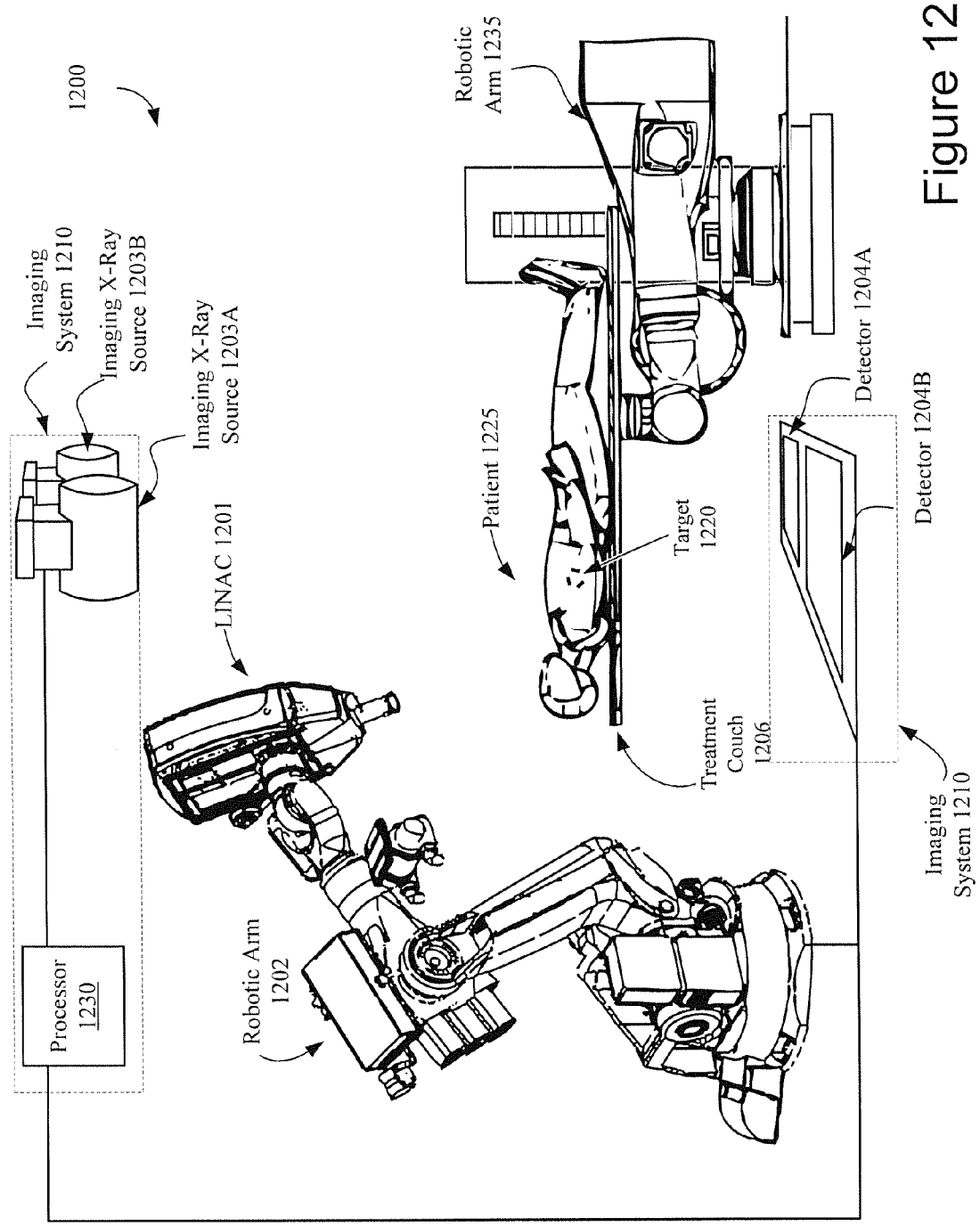
FIGS. 12 and 13 illustrate configurations of image-guided radiation treatment systems, in accordance with embodiments of the present invention.
Figure 13:
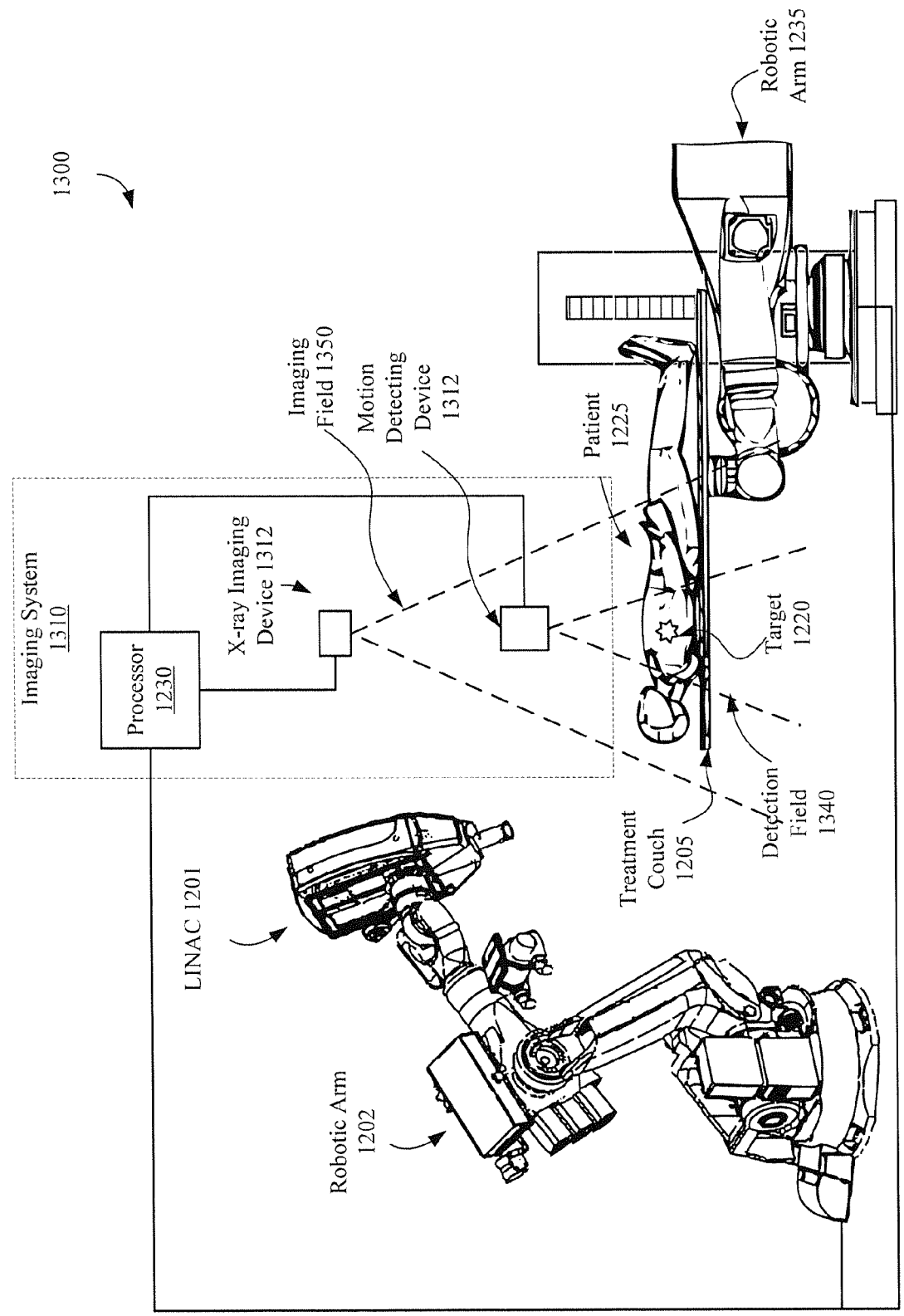

FIGS. 12 and 13 illustrate configurations of image-guided radiation treatment systems 1200 and 1300, in accordance with embodiments of the present invention. In the illustrated embodiments, the radiation treatment systems 1200 and 1300 include a linear accelerator (LINAC) 1201 that acts as a radiation treatment source. The LINAC 1201 is mounted on the end of a robotic arm 1202 having multiple (e.g., 5 or more) degrees of freedom in order to position the LINAC 1201 to irradiate a pathological anatomy (e.g., target 1220) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 1201 may be mounted on a gantry based system to provide isocentric beam paths. In one particular embodiment, the IGRT system is the Vero SBRT System (referred to as TM200 in Japan), a joint product of Mitsubishi Heavy Industries Ltd., of Tokyo Japan and BrainLAB AG of Germany, that utilizes a rigid O-ring based gantry. Such an O-ring based gantry system is described in greater detail below with reference to FIG. 14.

The LINAC 1201 may be positioned at multiple different nodes (predefined positions at which the robot stops and radiation may be delivered) during treatment by moving the robotic arm 1202. At the nodes, the LINAC 1201 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated. For example, the number of nodes may vary from 50 to 300, or more preferably 15 to 100 nodes and the number of beams may vary from 1200 to 3200, or more preferably 50 to 300.

Referring to FIG. 12, radiation treatment system 1200, in accordance with one embodiment of the present invention, includes an imaging system 1210 having a processor 1230 connected with x-ray sources 1203A and 1203B and fixed x-ray detectors 1204A and 1204B. Alternatively, the x-ray sources 1203A, 1203B and/or x-ray detectors 1204A, 1204B may be mobile, in which case they may be repositioned to maintain alignment with the target 1220, or alternatively to image the target from different orientations or to acquire many x-ray images and reconstruct a three-dimensional (3D) cone-beam CT. In one embodiment the x-ray sources are not point sources, but rather x-ray source arrays, as would be appreciated by the skilled artisan. In one embodiment, LINAC 1201 serves as an imaging source (whether gantry or robot mounted), where the LINAC power level is reduced to acceptable levels for imaging.

Imaging system 1210 may perform computed tomography (CT) such as cone beam CT, and images generated by imaging system 1201 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. Imaging system 1210, thus, provides stereoscopic imaging of the target 1220 and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

Referring to FIG. 13, in alternative embodiments an imaging system 1310 includes a motion detection device 1312 to determine target motion, the motion detecting device 1312 having a detection field 1340. The motion detecting device 1312 may detect external patient motion (such as chest movement during respiration) that occurs within an imaging field 1350. The motion detecting device 1312 can be any sensor or other device capable of identifying target movement. The motion detecting device 1312, may be, for example an optical sensor such as a camera, a pressure sensor, an electromagnetic sensor, or some other sensor that can provide motion detection without delivering ionizing radiation to a user (e.g., a sensor other than an x-ray imaging system). In one embodiment, the motion detecting device 1312 acquires measurement data indicative of target motion in real-time. Alternatively, the measurement data may be acquired at a frequency that is higher (potentially substantially higher) than can be achieved or than is desirable with x-ray imaging (due to ionizing radiation delivered to the patient with each x-ray image). In one embodiment, the motion detecting device 1312 does not provide a high absolute position accuracy. Instead, the motion detecting device 1312 may provide sufficient relative position accuracy to detect patient movement and/or target movement.

In one embodiment, the motion detecting device 1312 is an optical system, such as a camera. The optical system may track the position of light-emitting diodes (LEDs) situated on patient 1225. Alternatively, the optical system may directly track a surface region of patient 1225, as distinguished from tracking LEDs on the patient. There may be a correlation between movement of the target and movement of the LEDs and/or surface region of the patient 1225. Based on the correlation, when motion of the LEDs and/or surface region is detected, it can be determined that the target 1220 has also moved sufficiently to require another diagnostic x-ray image to precisely determine the location of the target.

Figure 14:
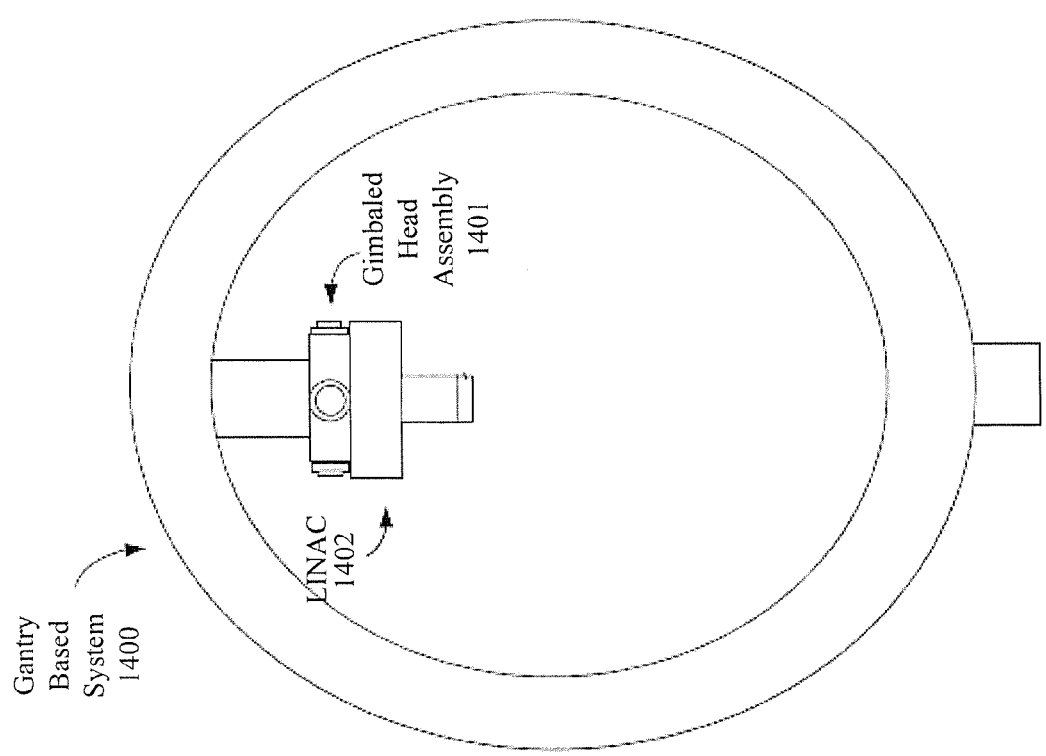
FIG. 14 illustrate a gantry based image-guided radiation treatment system, in accordance with embodiments of the present invention.

FIG. 14 illustrates one embodiment of a gantry based (isocentric) intensity modulated radiotherapy (IMRT) system 1400. In a gantry based system 1400, a radiation source (e.g., a LINAC) 1402 is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator (MLC) that allows portions of the beam to be blocked, so that the remaining beam incident on the patient has a pre-defined shape. The resulting system generates arbitrarily shaped radiation beams that intersect each other at the isocenter to deliver a dose distribution to the target.

In one embodiment, the gantry based system 1400 is an o-ring based system having a gimbaled radiation source head assembly 1401. The o-ring can be skewed around its vertical axis, and the gimbals can be driven to rotate in pan and tilt directions in order to position the linear accelerator 1402. In one embodiment, the gantry rotates 360 degrees about a horizontal axis, and additionally allows rotation about a vertical axis (a so called skew) of +/−60 degrees. Orthogonal gimbals hold the LINAC 1402, which allows pan and tilt motions of the LINAC. This system may include dual orthogonal imaging systems at 45 degrees from the treatment beam, to allow for the acquisition of x-ray images. In another embodiment, the gantry based system 1400 is a c-arm based system, as manufactured by Varian®.

It will be apparent from the foregoing description that aspects of the present invention may be embodied, at least in part, in software. That is, the techniques may be carried out in a computer system or other data processing system in response to its processor, such as digital processing system 1170, for example, executing sequences of instructions contained in a memory. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as digital processing system 1170.

A machine-readable medium can be used to store software and data which when executed by a general purpose or special purpose data processing system causes the system to perform various methods of the present invention. This executable software and data may be stored in various places including, for example, system memory and storage or any other device that is capable of storing software programs and/or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc.

Unless stated otherwise as apparent from the foregoing discussion, it will be appreciated that terms such as "processing," "computing," "generating," "comparing" "determining," "simulating," "testing," "identifying," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method comprising:
executing, by a processing device, a simulation treatment plan to simulate image guided treatment;
testing, by the processing device, an ability of one or more tracking methods to track a target position while simulating the image guided treatment;
presenting, by the processing device, simulation results to a user; and
of those tracking methods that will successfully track the target position during treatment delivery, ranking, by the processing device, the tracking methods based on accuracy and conformality of the tracking methods.

2. The method of claim 1, further comprising:
testing a plurality of the tracking methods; and
identifying an optimal tracking method from among the plurality of tracking methods based on the simulation results.

3. The method of claim 1, further comprising:
loading previously acquired images of the patient prior to simulating the image guided treatment, the previously generated images including at least one of a three-dimensional (3D) image or a four-dimensional (4D) study that includes target positions over a respiratory cycle of the patient;
creating a respiration model that describes target position as a function of external marker positions; and
using the previously acquired images and the respiration model to perform the testing.

4. The method of claim 3, wherein the external marker positions are associated with phases of the respiratory cycle.

5. The method of claim 3, wherein the images comprise a first 3D computed tomography (CT) image taken while the patient's breath is held in an inhale position and a second 3D CT image taken while the patient's breath is held in an exhale position.

6. The method of claim 3, wherein the images comprise a 4D computed tomography (CT) series consisting of multiple 3D CT images taken at different phases of the respiratory cycle.

7. The method of claim 3, wherein testing the ability of the one or more tracking methods to track the target position comprises:
generating an image data set that comprises a plurality of x-ray image pairs, each x-ray image pair comprising a first x-ray image having a first imaging plane and a second x-ray image having a second imaging plane; and
for each x-ray image in the image data set, computing a target position and correlating the target position with a digitally reconstructed radiograph (DRR) generated based on the previously acquired images and the respiration model.

8. The method of claim 7, further comprising:
for each x-ray image in the image data set that is successfully correlated, presenting a correlation result to a user and receiving a verification or a rejection of the correlation result from the user.

9. The method of claim 7, further comprising:
computing a confidence metric for each correlation; and
determining whether the correlation has failed based on the computed confidence metric.

10. The method of claim 7, wherein a tracking method has a high probability of successfully tracking the target position during treatment delivery if a threshold number of images from the image data set associated with that tracking method were successfully correlated.

11. The method of claim 1, wherein the image guided treatment comprises radiation treatment and the simulation treatment plan comprises a simulation radiation treatment plan, the method further comprising:
generating the simulation radiation treatment plan that is used to simulate the radiation treatment;
receiving a user selection of a tracking method after presenting the simulation results to the user; and
using the simulation radiation treatment plan and the selected tracking method to generate a radiation treatment plan.

12. The method of claim 1, further comprising:
receiving all tracking inputs necessary for the one or more tracking methods, wherein the tracking inputs comprise a delineation of the target and a delineation of a reference structure; and
creating an internal target volume that includes a motion range of the target.

13. A method of comprising:
executing, by a processing device, a simulation treatment plan to simulate image guided treatment;
testing, by the processing device, an ability of a plurality of tracking methods to track a target position while simulating the image guided treatment, wherein the tested tracking methods comprise at least one of a first tracking method that uses x-ray images from a first x-ray imaging device to track the target position in a first imaging plane, a second tracking method that uses x-ray images from a second x-ray imaging device to track the target position in a second imaging plane or a third tracking method that uses x-ray images from both the first x-ray imaging device and the second x-ray imaging device to track the target position in three dimensions; and
presenting, by the processing device, simulation results to a user.

14. The method of claim 13, further comprising:
identifying an optimal tracking method from among the plurality of tracking methods based on the simulation results.

15. An apparatus for performing treatment simulation, comprising:
a first x-ray imaging device and a second x-ray imaging device to generate positional data about a target; and
a processing device that includes instructions for performing the treatment simulation using a simulation radiation treatment plan, wherein the instructions cause the processing device to:
trigger the at least one detection device to generate the positional data;
test an ability of a plurality of tracking methods to track the target position based on the positional data, wherein the tested tracking methods comprise at least one of a first tracking method that uses x-ray images from the first x-ray imaging device to track the target position in a first imaging plane, a second tracking method that uses x-ray images from the second x-ray imaging device to track the target position in a second imaging plane or a third tracking method that uses x-ray images from both the first x-ray imaging device and the second x-ray imaging device to track the target position in three dimensions; and
present simulation results to a user.

16. The apparatus of claim 15, further comprising the instructions to cause the processing device to identify an optimal tracking method from among the plurality of tracking methods based on the simulation results.

17. The apparatus of claim 15, further comprising:
the processing device to load previously acquired images of the patient prior to performing the treatment simulation, wherein the instructions cause the processing device to create a respiration model that describes target position and target shape as a function of external marker positions and to use the previously acquired images and the respiration model to perform the test; and
an additional detection device to monitor the respiratory cycle of the patient while performing the treatment simulation.

18. The apparatus of claim 17, wherein the images comprise a first three-dimensional (3D) computed tomography (CT) image taken while the patient's breath is held in an inhale position and a second 3D CT image taken while the patient's breath is held in an exhale position.

19. The apparatus of claim 17, wherein to test the ability of the plurality of tracking methods, the processing device generates an image data set that comprises a plurality of x-ray image pairs, each x-ray image pair comprising a first x-ray image having the first imaging plane and a second x-ray image having the second imaging plane, and for each x-ray image in the image data set, the processing device computes a target position and correlates the target position with a digitally reconstructed radiograph (DRR) generated based on the previously acquired images and the respiration model.

20. The apparatus of claim 19, further comprising the instructions to cause the processing device to:
for each x-ray image in the image data set that is successfully correlated, present a correlation result to a user and receive a verification or a rejection of the correlation result from the user.

21. The apparatus of claim 19, further comprising the instructions to cause the processing device to:
compute a confidence metric for each correlation; and
determine whether the correlation has failed based on the computed confidence metric.

22. The apparatus of claim 19, wherein a tracking method has a high probability of successfully tracking the target position during treatment delivery if a threshold number of images from the image data set associated with that tracking method were successfully correlated.

23. The apparatus of claim 15, further comprising the instructions to cause the processing device to:
generate the simulation radiation treatment plan that is used to simulate the treatment;
receive a user selection of a tracking method after presenting the simulation results to the user; and
use the simulation radiation treatment plan and the selected tracking method to generate a radiation treatment plan.

24. The apparatus of claim 15, further comprising the instructions to cause the processing device to:

receive all tracking inputs necessary for the plurality of tracking methods, wherein the tracking inputs comprise a delineation of the target and a delineation of a reference structure; and create an internal target volume that includes a motion range of the target.

25. The apparatus of claim 15, wherein the instructions further cause the processing device to analyze the simulation results to determine whether any of the plurality of tracking methods will successfully track the target position during treatment delivery.

26. An apparatus for performing treatment simulation, comprising:

at least one detection device to generate positional data about a target; and a processing device that includes instructions for performing the treatment simulation using a simulation radiation treatment plan, wherein the instructions cause the processing device to:

trigger the at least one detection device to generate the positional data;

test an ability of one or more tracking methods to track the target position based on the positional data;

present simulation results to a user; and of those tracking methods that will successfully track the target position during treatment delivery, rank the tracking methods based on accuracy and conformality of the tracking methods.

27. The apparatus of claim 26, further comprising the instructions to cause the processing device to test a plurality of tracking methods and to identify an optimal tracking method from among the plurality of tracking methods based on the simulation results.

* * * * *